United States Patent
Pingleton et al.

(10) Patent No.: US 8,636,759 B2
(45) Date of Patent: Jan. 28, 2014

(54) BLADELESS OBTURATOR

(75) Inventors: Edward D. Pingleton, San Juan Capistrano, CA (US); Matthew A. Wixey, Rancho Santa Margarita, CA (US); Henry Kahle, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 166 days.

(21) Appl. No.: 12/750,372

(22) Filed: Mar. 30, 2010

(65) Prior Publication Data
US 2010/0222801 A1 Sep. 2, 2010

Related U.S. Application Data

(63) Continuation of application No. 10/489,403, filed as application No. PCT/US02/06759 on Mar. 4, 2002, now Pat. No. 7,686,823.

(60) Provisional application No. 60/324,613, filed on Sep. 24, 2001.

(51) Int. Cl.
*A61B 17/34* (2006.01)
(52) U.S. Cl.
USPC .......................................................... 606/185
(58) Field of Classification Search
USPC ............. 606/79, 80, 159, 167, 170, 180, 185; 408/83.5, 227, 229, 230; 600/564–568
See application file for complete search history.

(56) References Cited

U.S. PATENT DOCUMENTS

| RE682 E | 4/1859 | Peale |
|---|---|---|
| 184,573 A | 11/1876 | Becker |
| 207,932 A | 9/1878 | Alvord |

(Continued)

FOREIGN PATENT DOCUMENTS

| BE | 1 006 811 | 12/1994 |
|---|---|---|
| BE | 1006811 A6 | 12/1994 |

(Continued)

OTHER PUBLICATIONS

Karl Storz, The Karl Storz Ternamian EndoTIP (TM) System.

(Continued)

*Primary Examiner* — Anu Ramana
(74) *Attorney, Agent, or Firm* — Rimas T. Lukas; Pui Tong Ho

(57) ABSTRACT

A surgical obturator adapted to penetrate a body wall includes an elongate shaft having an axis which extends between a proximal end and a distal end. A bladeless tip, disposed at the distal end of the shaft has an outer surface which extends to a blunt point The outer surface has a pair of side sections separated by an intermediate section The side sections extend from the blunt point radially outwardly with progressive positions proximally along the axis. These side sections include a distal portion in proximity to the blunt point, and a proximal portion in proximity to the shaft. The distal portion of the side section is twisted radially with respect to the proximal portion of the side section. The outer surface in radial cross section has the general configuration of a geometric shape which rotates in a first direction about the axis with progressive proximal radial cross sections along the axis.

24 Claims, 13 Drawing Sheets

(56) References Cited

U.S. PATENT DOCUMENTS

| | | | |
|---|---|---|---|
| 224,513 | A | 2/1880 | Burdon |
| 396,754 | A | 1/1889 | Mayfield |
| 764,322 | A | 7/1904 | Wiegand |
| 1,147,408 | A | 7/1915 | Kelis |
| 1,672,258 | A | 6/1928 | Hippenmeyer |
| 1,727,495 | A | 9/1929 | Wappler |
| 1,845,727 | A | 2/1932 | Slaughter |
| 2,102,274 | A | 12/1937 | Larimore |
| 2,189,343 | A | 2/1940 | Fritz |
| 2,301,338 | A | 11/1942 | Smith |
| 2,434,594 | A | 1/1948 | Schultz |
| 2,441,143 | A | 5/1948 | Gracey |
| 2,646,701 | A | 7/1953 | Lietin |
| 2,699,770 | A | 1/1955 | Fourestier et al. |
| 2,764,148 | A | 9/1956 | Sheldon |
| 2,764,149 | A | 9/1956 | Sheldon |
| 2,769,355 | A | 11/1956 | Henry |
| 2,877,368 | A | 3/1959 | Sheldon |
| 2,887,136 | A * | 5/1959 | Rathgeber ............... 144/219 |
| 2,932,294 | A | 4/1960 | Fourestier et al. |
| 3,005,468 | A | 10/1961 | Erwin et al. |
| 3,021,834 | A | 2/1962 | Sheldon |
| 3,033,226 | A | 5/1962 | Allen |
| 3,042,022 | A | 7/1962 | Sheldon |
| 3,224,320 | A | 12/1965 | Knudsen |
| 3,277,922 | A | 10/1966 | Eisel |
| 3,279,460 | A | 10/1966 | Sheldon |
| 3,357,433 | A | 12/1967 | Fourestier et al. |
| 3,385,553 | A | 5/1968 | Braun |
| 3,417,745 | A | 12/1968 | Sheldon |
| 3,437,747 | A | 4/1969 | Sheldon |
| 3,459,189 | A | 8/1969 | Alley et al. |
| 3,556,085 | A | 1/1971 | Takahashi |
| 3,613,684 | A | 10/1971 | Sheridan |
| 3,653,338 | A | 4/1972 | Sauey |
| 3,791,379 | A | 2/1974 | Storz |
| 3,817,251 | A | 6/1974 | Hasson |
| 3,821,956 | A | 7/1974 | Gordhamer |
| 3,870,036 | A | 3/1975 | Fiore |
| 3,961,621 | A | 6/1976 | Northeved |
| 3,971,385 | A | 7/1976 | Corbett |
| 3,994,287 | A | 11/1976 | Turp |
| 3,994,301 | A | 11/1976 | Agris |
| 4,028,987 | A | 6/1977 | Wilson |
| 4,112,932 | A | 9/1978 | Chiulli |
| 4,126,291 | A | 11/1978 | Gilbert et al. |
| 4,150,929 | A | 4/1979 | Brandt |
| 4,168,882 | A | 9/1979 | Hopkins |
| 4,180,068 | A | 12/1979 | Jacobsen et al. |
| 4,191,191 | A | 3/1980 | QAubum |
| 4,222,375 | A | 9/1980 | Martinez |
| 4,248,214 | A | 2/1981 | Hannah et al. |
| 4,254,762 | A | 3/1981 | Yoon |
| 4,269,192 | A | 5/1981 | Matsuo |
| 4,274,771 | A | 6/1981 | Nishimura |
| 4,285,618 | A | 8/1981 | Shanley |
| 4,299,230 | A | 11/1981 | Kubota |
| 4,311,138 | A | 1/1982 | Sugarman |
| 4,319,563 | A | 3/1982 | Kubota |
| 4,356,826 | A | 11/1982 | Kubota |
| 4,386,179 | A | 5/1983 | Sterling |
| 4,414,966 | A | 11/1983 | Stednitz |
| 4,429,856 | A | 2/1984 | Jackson |
| 4,436,519 | A | 3/1984 | O'Neill |
| 4,480,949 | A * | 11/1984 | Van De Bogart ............... 407/54 |
| 4,493,444 | A | 1/1985 | Deli et al. |
| 4,498,902 | A | 2/1985 | Ash et al. |
| 4,524,805 | A | 6/1985 | Hoffman |
| 4,535,773 | A | 8/1985 | Yoon |
| 4,535,808 | A | 8/1985 | Johanson et al. |
| 4,537,593 | A | 8/1985 | Alchas |
| 4,567,882 | A | 2/1986 | Heller |
| 4,601,710 | A | 7/1986 | Moll |
| 4,750,877 | A | 6/1988 | McFarlane |
| 4,762,130 | A | 8/1988 | Fogarty et al. |
| 4,779,613 | A | 10/1988 | Hashiguchi et al. |
| 4,803,999 | A | 2/1989 | Liegner |
| 4,813,400 | A | 3/1989 | Washizuka et al. |
| 4,850,393 | A | 7/1989 | Lashomb |
| 4,895,431 | A | 1/1990 | Tsujluchi et al. |
| 4,901,142 | A | 2/1990 | Ikuno et al. |
| 4,956,143 | A | 9/1990 | McFarlane |
| 4,959,067 | A | 9/1990 | Muller |
| 4,972,827 | A | 11/1990 | Kishi et al. |
| 4,978,350 | A | 12/1990 | Wagenknecht |
| 5,017,057 | A | 5/1991 | Kruygor |
| 5,030,210 | A | 7/1991 | Alchas |
| 5,041,100 | A | 8/1991 | Rowland et al. |
| 5,057,082 | A | 10/1991 | Burchette, Jr. |
| 5,066,288 | A | 11/1991 | Deniego et al. |
| 5,098,379 | A | 3/1992 | Conway |
| 5,098,388 | A | 3/1992 | Kulkashi et al. |
| 5,104,316 | A | 4/1992 | McSpadden |
| 5,104,388 | A | 4/1992 | Quackenbush |
| 5,104,389 | A | 4/1992 | Deem et al. |
| 5,114,407 | A * | 5/1992 | Burbank ............... 604/164.12 |
| 5,116,547 | A | 5/1992 | Tsukahara et al. |
| 5,147,376 | A | 9/1992 | Pianetti |
| 5,159,920 | A | 11/1992 | Condon et al. |
| 5,163,941 | A | 11/1992 | Garth et al. |
| 5,178,186 | A | 1/1993 | Levasseur |
| 5,186,972 | A | 2/1993 | Williams et al. |
| 5,197,955 | A | 3/1993 | Stephens et al. |
| 5,207,656 | A | 5/1993 | Kranys |
| 5,217,441 | A | 6/1993 | Shichman |
| 5,221,163 | A | 6/1993 | Nishimura |
| 5,240,397 | A | 8/1993 | Fay et al. |
| 5,246,425 | A | 9/1993 | Hunsberger et al. |
| 5,250,068 | A | 10/1993 | Ideguchi et al. |
| 5,256,149 | A | 10/1993 | Banik et al. |
| 5,258,003 | A | 11/1993 | Ciaglia |
| 5,269,316 | A | 12/1993 | Spitainy |
| 5,271,380 | A | 12/1993 | Riek et al. |
| 5,279,567 | A | 1/1994 | Ciaglia et al. |
| 5,288,290 | A | 2/1994 | Brody |
| 5,290,276 | A | 3/1994 | Sewell |
| 5,290,585 | A | 3/1994 | Elton |
| 5,300,033 | A | 4/1994 | Miller |
| 5,334,150 | A | 8/1994 | Kaali |
| 5,342,382 | A | 8/1994 | Brinkerhoff |
| 5,350,364 | A | 9/1994 | Stephens et al. |
| 5,370,624 | A | 12/1994 | Edwards et al. |
| 5,372,588 | A * | 12/1994 | Farley et al. ............... 604/170.01 |
| 5,374,253 | A | 12/1994 | Burns, Sr. et al. |
| 5,380,291 | A | 1/1995 | Kaali |
| 5,387,197 | A | 2/1995 | Smith |
| 5,389,077 | A | 2/1995 | Melinyshin et al. |
| 5,391,153 | A | 2/1995 | Haber et al. |
| 5,391,248 | A | 2/1995 | Brain |
| 5,392,766 | A | 2/1995 | Masterson et al. |
| 5,405,328 | A | 4/1995 | Vidal et al. |
| 5,407,427 | A | 4/1995 | Zhu et al. |
| 5,431,151 | A | 7/1995 | Riek et al. |
| 5,441,041 | A | 8/1995 | Sauer et al. |
| 5,443,484 | A | 8/1995 | Kirsch et al. |
| 5,445,615 | A | 8/1995 | Yoon et al. |
| 5,454,791 | A | 10/1995 | Tovey et al. |
| 5,480,410 | A | 1/1996 | Cuschieri et al. |
| 5,510,065 | A | 4/1996 | McFarlane |
| 5,540,711 | A | 7/1996 | Kieturakis et al. |
| 5,542,845 | A | 8/1996 | Jenkins |
| 5,549,546 | A | 8/1996 | Schneider et al. |
| 5,551,947 | A | 9/1996 | Kaali |
| 5,562,696 | A | 10/1996 | Nobles et al. |
| 5,569,291 | A | 10/1996 | Privitera |
| 5,569,292 | A | 10/1996 | Scwemberger et al. |
| 5,577,993 | A | 11/1996 | Zhu et al. |
| 5,591,186 | A | 1/1997 | Wurster et al. |
| 5,591,192 | A | 1/1997 | Privitera et al. |
| 5,593,402 | A | 1/1997 | Patrick |
| 5,603,720 | A | 2/1997 | Kieturakis |
| 5,609,562 | A | 3/1997 | Kaali |
| 5,609,604 | A | 3/1997 | Schwemberger et al. |
| 5,613,954 | A | 3/1997 | Nelson et al. |

(56) References Cited

U.S. PATENT DOCUMENTS

| | | |
|---|---|---|
| 5,622,462 A | 4/1997 | Gakhar et al. |
| 5,630,805 A | 5/1997 | Ternamian |
| 5,634,908 A | 6/1997 | Loomas |
| 5,658,236 A | 8/1997 | Sauer |
| 5,662,615 A | 9/1997 | Blake, III |
| 5,662,673 A | 9/1997 | Kieturakis |
| 5,676,611 A | 10/1997 | Foster |
| 5,685,820 A | 11/1997 | Riek et al. |
| 5,695,462 A | 12/1997 | Sutcu et al. |
| 5,697,947 A | 12/1997 | Wolf |
| 5,720,730 A | 2/1998 | Blake, III |
| 5,720,761 A | 2/1998 | Kaali |
| 5,735,867 A | 4/1998 | Golser et al. |
| 5,738,628 A | 4/1998 | Sierocuk |
| 5,743,881 A | 4/1998 | Demco |
| 5,746,734 A | 5/1998 | Dormandy, Jr. et al. |
| 5,752,970 A | 5/1998 | Yoon et al. |
| 5,759,185 A | 6/1998 | Grinberg |
| 5,779,697 A | 7/1998 | Glowa et al. |
| 5,785,693 A | 7/1998 | Halning |
| 5,792,112 A | 8/1998 | Hart et al. |
| 5,797,888 A | 8/1998 | Yoon et al. |
| 5,797,944 A | 8/1998 | Nobeles et al. |
| 5,817,061 A | 10/1998 | Goodwin et al. |
| 5,817,062 A | 10/1998 | Flom et al. |
| 5,836,957 A | 11/1998 | Schulz |
| 5,842,971 A | 12/1998 | Yoon |
| 5,860,996 A | 1/1999 | Urban et al. |
| 5,871,474 A | 2/1999 | Hermann et al. |
| 5,876,202 A | 3/1999 | Berlin |
| 5,884,639 A | 3/1999 | Chen |
| 5,891,013 A | 4/1999 | Thompson |
| 5,893,865 A | 4/1999 | Swindle |
| 5,904,699 A | 5/1999 | Schwemberger et al. |
| 5,913,818 A | 6/1999 | Co et al. |
| 5,922,351 A | 7/1999 | Daher |
| 5,924,452 A | 7/1999 | Szpara et al. |
| 5,941,852 A | 8/1999 | Dunlap et al. |
| 5,957,884 A | 9/1999 | Hooven |
| 5,957,888 A | 9/1999 | Hinchliffe |
| 5,968,060 A | 10/1999 | Kellogg |
| 5,976,079 A | 11/1999 | Volz et al. |
| 5,976,168 A | 11/1999 | Chin |
| 5,980,809 A | 11/1999 | Crain et al. |
| 5,984,941 A | 11/1999 | Wilson |
| 6,001,084 A | 12/1999 | Riek |
| 6,007,481 A | 12/1999 | Riek et al. |
| 6,019,776 A | 2/2000 | Preissman |
| 6,024,551 A | 2/2000 | Yamaguchi |
| 6,030,406 A | 2/2000 | Davis |
| 6,043,310 A | 3/2000 | Liu et al. |
| 6,053,194 A | 4/2000 | Nelson et al. |
| 6,068,637 A | 5/2000 | Popov et al. |
| 6,077,481 A | 6/2000 | Ichida et al. |
| 6,092,551 A | 7/2000 | Bennett |
| 6,168,355 B1 | 1/2001 | Wardell |
| 6,179,528 B1 | 1/2001 | Wardell |
| 6,203,559 B1 | 3/2001 | Davis |
| 6,203,745 B1 | 3/2001 | Wachsmann et al. |
| 6,221,061 B1 | 4/2001 | Engelson et al. |
| 6,228,059 B1 | 5/2001 | Astarita |
| 6,228,063 B1 | 5/2001 | Aboul-Hosn |
| 6,270,484 B1 | 8/2001 | Yoon |
| 6,302,873 B1 | 10/2001 | Moenning |
| 6,319,266 B1 | 11/2001 | Stellon |
| 6,355,014 B1 | 3/2002 | Zadno-Azizi et al. |
| 6,387,043 B1 | 5/2002 | Yoon |
| 6,462,111 B1 | 10/2002 | Singh et al. |
| 6,468,228 B1 | 10/2002 | Topel et al. |
| 6,478,806 B2 | 11/2002 | McFarlane |
| 6,508,759 B1 | 1/2003 | Taylor et al. |
| 6,520,939 B2 | 2/2003 | Lafontaine |
| 6,579,298 B1 * | 6/2003 | Bruneau et al. ............... 606/159 |
| 6,656,160 B1 | 12/2003 | Taylor et al. |
| 6,656,198 B2 | 12/2003 | Tsonton et al. |
| 6,685,630 B2 | 2/2004 | Sauer et al. |
| 6,764,107 B1 | 7/2004 | Obahi et al. |
| 6,770,731 B2 | 8/2004 | Mason et al. |
| 6,835,201 B2 | 12/2004 | O'Heeron |
| 6,884,253 B1 | 4/2005 | McFarlane |
| 6,887,194 B2 | 5/2005 | Hart et al. |
| 6,902,541 B2 | 6/2005 | McNally et al. |
| 6,939,296 B2 | 9/2005 | Ewers et al. |
| 7,008,979 B2 | 3/2006 | Schottman et al. |
| 7,037,303 B2 | 5/2006 | Beaufore et al. |
| 7,056,294 B2 | 6/2006 | Khairkhahan et al. |
| 7,056,329 B2 | 6/2006 | Kerr |
| 7,070,586 B2 | 7/2006 | Hart et al. |
| 7,182,752 B2 | 2/2007 | Stubbs et al. |
| 7,344,519 B2 | 3/2008 | Wing et al. |
| 7,370,709 B2 | 5/2008 | Williamson, Jr. |
| 7,470,255 B2 | 12/2008 | Sterns et al. |
| 7,563,250 B2 | 7/2009 | Wenchell |
| 7,686,823 B2 | 3/2010 | Pingleton et al. |
| 7,708,713 B2 | 5/2010 | Albrecht et al. |
| 7,758,603 B2 | 7/2010 | Taylor et al. |
| 7,794,644 B2 | 9/2010 | Taylor et al. |
| 7,811,253 B2 | 10/2010 | Hart et al. |
| 7,942,862 B2 | 5/2011 | Hart et al. |
| 7,947,058 B2 | 5/2011 | Kahle et al. |
| 8,007,477 B2 | 8/2011 | Johnson et al. |
| 8,028,395 B2 | 10/2011 | Taylor et al. |
| 8,105,285 B2 | 1/2012 | Hart et al. |
| 8,152,828 B2 | 4/2012 | Taylor et al. |
| 8,282,663 B2 | 10/2012 | Smith |
| 8,317,815 B2 | 11/2012 | Mastri et al. |
| 2002/0013597 A1 | 1/2002 | McFarlane |
| 2002/0026207 A1 | 2/2002 | Stellon et al. |
| 2002/0133188 A1 | 9/2002 | O'Heeron et al. |
| 2002/0183715 A1 | 12/2002 | Mantell et al. |
| 2002/0183775 A1 | 12/2002 | Tsonton et al. |
| 2003/0023201 A1 | 1/2003 | Aboul-Hosn |
| 2003/0032755 A1 | 2/2003 | Gomey et al. |
| 2003/0059263 A1 | 3/2003 | Chen |
| 2003/0187471 A1 | 10/2003 | Cooper |
| 2004/0015185 A1 | 1/2004 | Ewers et al. |
| 2004/0082969 A1 | 4/2004 | Kerr |
| 2004/0093000 A1 | 5/2004 | Kerr |
| 2004/0093018 A1 | 5/2004 | Johnson et al. |
| 2004/0106942 A1 | 6/2004 | Taylor et al. |
| 2004/0108623 A1 | 6/2004 | Deeter et al. |
| 2004/0167559 A1 | 8/2004 | Taylor et al. |
| 2004/0199127 A1 | 10/2004 | Jensen et al. |
| 2004/0204671 A1 | 10/2004 | Stubbs et al. |
| 2004/0230155 A1 | 11/2004 | Blanco et al. |
| 2004/0230217 A1 | 11/2004 | O'Heeron |
| 2004/0254517 A1 | 12/2004 | Quiroz-Mercado et al. |
| 2005/0033237 A1 | 2/2005 | Fentress et al. |
| 2005/0033246 A1 | 2/2005 | Ahlberg et al. |
| 2005/0038466 A1 | 2/2005 | O'Heeron et al. |
| 2005/0059865 A1 | 3/2005 | Kahle |
| 2005/0065543 A1 | 3/2005 | Kahle et al. |
| 2005/0070850 A1 | 3/2005 | Albrecht |
| 2005/0107803 A1 | 5/2005 | Guanche |
| 2005/0107816 A1 | 5/2005 | Pingleton et al. |
| 2005/0113533 A1 | 5/2005 | Shaikh et al. |
| 2005/0149094 A1 | 7/2005 | Kasahara et al. |
| 2005/0149096 A1 | 7/2005 | Hilal et al. |
| 2005/0159711 A1 | 7/2005 | Kathrani et al. |
| 2005/0216028 A1 | 9/2005 | Hart et al. |
| 2005/0227610 A1 | 10/2005 | Zukor et al. |
| 2005/0251191 A1 | 11/2005 | Taylor et al. |
| 2005/0273133 A1 | 12/2005 | Shluzas et al. |
| 2005/0283122 A1 | 12/2005 | Nordgren |
| 2005/0288622 A1 | 12/2005 | Albrecht et al. |
| 2006/0030755 A1 | 2/2006 | Ewers et al. |
| 2006/0041270 A1 | 2/2006 | Lenker et al. |
| 2006/0047284 A1 | 3/2006 | Gresham |
| 2006/0058570 A1 | 3/2006 | Rapach et al. |
| 2006/0074374 A1 | 4/2006 | Gresham |
| 2006/0118189 A1 | 6/2006 | Tekulve et al. |
| 2006/0224174 A1 | 10/2006 | Smith et al. |
| 2006/0264991 A1 | 11/2006 | Johnson |
| 2007/0027453 A1 | 2/2007 | Hart et al. |

(56) References Cited

U.S. PATENT DOCUMENTS

| | | |
|---|---|---|
| 2007/0075465 A1 | 4/2007 | Taylor et al. |
| 2007/0088277 A1 | 4/2007 | McGinley |
| 2007/0239108 A1 | 10/2007 | Albrecht et al. |
| 2008/0065021 A1 | 3/2008 | Jenkins et al. |
| 2008/0086074 A1 | 4/2008 | Taylor et al. |
| 2008/0086093 A1 | 4/2008 | Steppe et al. |
| 2009/0137943 A1 | 5/2009 | Stearns et al. |
| 2010/0025045 A1 | 2/2010 | Lake et al. |

FOREIGN PATENT DOCUMENTS

| | | |
|---|---|---|
| CA | 2 170 841 | 9/1997 |
| DE | 0365049 | 12/1922 |
| DE | 1616107 | 4/1971 |
| DE | 2218901 | 10/1973 |
| DE | 2538758 | 3/1977 |
| DE | 2929233 | 1/1980 |
| DE | 2922239 | 12/1980 |
| DE | 4020956 | 1/1991 |
| DE | 41 33 073 A1 | 4/1992 |
| DE | 4133073 | 4/1992 |
| DE | 4035146 | 5/1992 |
| DE | 4116648 | 11/1992 |
| DE | 29521431 | 4/1997 |
| DE | 19541041 | 5/1997 |
| DE | 19718086 | 11/1998 |
| DE | 19819432 | 11/1999 |
| EP | 0135364 | 3/1985 |
| EP | 0312787 | 4/1989 |
| EP | 0347140 | 12/1989 |
| EP | 0369936 | 5/1990 |
| EP | 0369937 | 5/1990 |
| EP | 0474124 | 3/1992 |
| EP | 548612 | 6/1993 |
| EP | 0556056 | 8/1993 |
| EP | 0 724 864 | 8/1996 |
| EP | 0724864 | 8/1996 |
| EP | 1582158 | 10/2005 |
| EP | 2229897 | 9/2010 |
| EP | 2233090 | 9/2010 |
| FR | 1370580 | 8/1964 |
| GB | 186 005 | 9/1922 |
| GB | 2 124 970 | 2/1984 |
| GB | 186 005 | 9/1992 |
| GB | 2 313 316 | 11/1997 |
| JP | 408127661 | 5/1996 |
| JP | 2001-137253 | 5/2001 |
| SU | 0942730 | 7/1982 |
| SU | 1328658 | 8/1987 |
| SU | 1329769 | 8/1987 |
| WO | WO 93/25148 | 12/1993 |
| WO | WO 98/33536 | 2/1994 |
| WO | WO 96/01132 | 1/1996 |
| WO | WO 96/10361 | 4/1996 |
| WO | WO 97/40758 | 11/1997 |
| WO | WO 99/02089 | 1/1999 |
| WO | WO 99/15084 | 4/1999 |
| WO | WO 00/18306 | 4/2000 |
| WO | WO 00/54648 | 9/2000 |
| WO | WO 02/01998 | 1/2002 |
| WO | WO 02/01998 A2 | 1/2002 |
| WO | WO 01/08563 | 2/2002 |
| WO | WO 02/34108 | 5/2002 |
| WO | WO 03/026512 | 4/2003 |
| WO | WO 03/026512 A1 | 4/2003 |
| WO | WO 03/032819 | 4/2003 |
| WO | WO 03/096879 | 11/2003 |
| WO | WO 03/096879 A2 | 11/2003 |
| WO | WO 03/096879 A3 | 11/2003 |
| WO | WO 2004/037097 | 5/2004 |
| WO | WO 2004/093699 | 11/2004 |
| WO | WO 2005/063134 | 7/2005 |
| WO | WO 2005/063134 A1 | 7/2005 |
| WO | WO 2007/093957 | 8/2007 |

OTHER PUBLICATIONS

Karl Storz, Zerocart Trocar with eccentric tip, Recklinghausen, Germany.
Ethicon Endo-Surgery, Inc., Endopath Minimally Invasive Access.
Co-Pending U.S Appl. No. 11/170,567, filed Jun. 29, 2005; Title: Insufflating Optical Surgical Instrument.
Co-Pending U.S Appl. No. 10/514,313, filed Nov. 12, 2004; Title: Blunt Tip Obturator.
Co-Pending U.S. Appl. No. 10/956,167, filed Oct. 3, 2003; Title: Bladeless Optical Obturator.
U.S. Appl. No. 10/745,262, filed Dec. 23, 2003; Title: Catheter With Conduit Traversing Tip.
Co-Pending U.S. Appl. No. 11/868,883, filed Oct. 8, Visual Insufflation Port.
Co Pending U.S. Appl. No. 10/805,864, filed Mar. 22, 2004; Title: Surgical Access Port and Method.
European Patent Office, Supplementary European Search Report for European Patent Application No. 02 706494 8 and PCT International Application No. PCT/US02/06759 dated Jul. 2, 2008.
European Patent Office, European Search Report for European Application No. 11 19 1193 dated Mar. 5, 2012 entitled Bladeless Obturator.
European Patent Office, European Search Report for European Application No. 11 19 1184.8 dated Feb. 23, 2012 entitled Bladeless Obturator.
European Patent Office, European Search Report for European Application No. 11 19 1189.7 dated Feb. 24, 2012 entitled Bladeless Obturator.
European Patent Office, European Search Report for European Application No. 11 19 1191 dated Feb. 29, 2012 entitled Bladeless Obturator.
European Patent Office, European Search Report for European Application No. 11 19 1179 dated Feb. 21, 2012 entitled Bladeless Obturator.
European Patent Office, European Search Report for European Application No. 11 19 1187 dated Feb. 23, 2012 entitled Bladeless Obturator.
European Patent Office, European Search Report for European Application No. 11 19 1175.6 dated Feb. 21, 2012 entitled Bladeless Obturator.
U.S. Appl. No. 10/745,262, filed Dec. 23, 2003; Title: "Catheter With Conduit Traversing Tip" (abandoned).
Co-Pending U.S. Appl. No. 12/750,372, filed Mar. 30, 2010, title: "Bladeless Obturator".
Co-Pending U.S. Appl. No. 11/549,872, filed Oct. 16, 2006, title: "Surgical Devices, Systems and Methods Thereof Having Gel Material, Gel Coatings, or Gel Lubricants".
Co-Pending U.S. Appl. No. 13/565,972, filed Aug. 3, 2012, title: "Bladeless Optical Obturator".
Co-Pending U.S. Appl. No. 13/356,260, filed Jan. 23, 2012, title: "Insufflating Optical Surgical Instrument".
Co-Pending U.S. Appl. No. 13/078,750, filed Apr. 1, 2011 title "Surgical Access Apparatus and Method".
Co-Pending U.S. Appl. No. 12/569,652, filed Sep. 29, 2009; title "First-Entry Trocar System".
Co-Pending U.S. Appl. No. 12/359,964, filed Jan. 26, 2009; title: "Insufflating Access System".
Co-Pending U.S. Appl. No. 13/462,330, filed May 2, 2012; title: "Low-Profile Surgical Universal Access Port".
Co-Pending U.S. Appl. No. 13/411,244, filed Mar. 2, 2012; title: "Blunt Tip Obturator".
Co-Pending U.S. Appl. No. 13/586,825, filed Aug. 15, 2012; title: "Blunt Tip Obturator".
Co-Pending U.S. Appl. No. 11/868,883, filed Oct. 8, 2007; Title: "Visual Insufflation Port".
International Bureau of WIPO, International Preliminary Report on Patentability for International Application No. PCT/US04/032346, dated May 20, 2008.
International Bureau of WIPO, International Preliminary Report on Patentability for International Application No. PCT/US2005/022716 mailed Nov. 22, 2005.

(56) References Cited

OTHER PUBLICATIONS

International Bureau of WIPO, International Preliminary Report on Patentability for International Application No. PCT/US2006/060013, mailed Apr. 24, 2008.
International Bureau of WIPO, The International Preliminary Report on Patentability for International Application No. PCT/US2009/058792, titled First Entry Trocar System, dated Mar. 29, 2011.
International Bureau of WIPO, The International Preliminary Report on Patentability for International Application No. PCT/US2007/080724, titled "Visual Insufflation Port", dated Apr. 7, 2009.
International Bureau of WIPO, The International Preliminary Report on Patentability for International Application No. PCT/US2009/32026, titled "Insufflating Access System", dated Jul. 27, 2010.
International Bureau of WIPO, The International Preliminary Report on Patentability for International Application No. PCT/US2004/000695, titled "Surgical Access Apparatus and Method", dated Jul. 22, 2005.
International Bureau of WIPO, The International Preliminary Report on Patentability for International Application No. PCT/US2004/04883, titled "Surgical Access Apparatus and Method", dated Sep. 9, 2005.
International Searching Authority, International Search Report and Written Opinion for International Application No. PCT/US2004/000695, titled "Surgical Access Apparatus and Method", mailed Jan. 12, 2005.
International Searching Authority, International Search Report and Written Opinion for International Application No. PCT/US2004/04883, titled "Surgical Access Apparatus and Method", mailed Mar. 31, 2005.
International Searching Authority, International Search Report and Written Opinion for International Application No. PCT/US2002/06759, titled "Bladeless Obturator", mailed Jul. 12, 2002.
International Searching Authority, International Search Report and Written Opinion for International Application No. PCT/US2005/022716, titled "Insufflating Optical Surgical Instrument", mailed Nov. 22, 2005.
International Searching Authority, International Search Report and Written Opinion for International Application No. PCT/US04/32346, titled Bladeless Optical Obturator, mailed May 20, 2008.
International Searching Authority, International Search Report and Written Opinion for International Application No. PCT/US2009/32026, titled "Insufflating Access System", mailed Mar. 23, 2009.
International Searching Authority, International Search Report and Written Opinion for International Application No. PCT/US2007/080724, titled "Visual Insufflation Port", mailed Apr. 16, 2008.
International Searching Authority/US, International Search Report and The Written Opinion of the International Searching Authority dated May 27, 2009, for International Application No. PCT/US2009/037863, titled "Instrument Seal with Inverting Shroud", mailed May 27, 2009.
The International Searching Authority, The International Search Report and the Written Opinion for International Application No. PCT/US2009/058792, titled "First Entry Trocar System", mailed Dec. 23, 2009.
International Searching Authority, International Search Report and Written Opinion for International Application No. PCT/US2012/036119, title "Low-Profile Surgical Universal Access Port", mailed Nov. 7, 2012.

European Patent Office, Supplementary European Search Report for European Patent Application No. EP 02706494.8, titled "Bladeless Obturator", dated Jun. 24, 2008.
European Patent Office, Supplementary European Search Report for European Patent Application No. EP 03753017.7, titled "Blunt Tip Obturator", dated Nov. 21, 2008.
European Patent Office, Supplementary European Search Report for European Patent Application No. EP 047122378, titled "Surgical Access Apparatus and Method", dated May 19, 2008.
European Patent Office, Supplementary European Search Report for European Patent Application No. EP 07843973.4, titled "Visual Insufflation Port" dated Oct. 4, 2008.
European Patent Office, Supplementary European Search Report for European Patent Application No. EP 04793965.7, titled "Bladeless Optical Obturator", dated Apr. 16, 2010.
European Patent Office, Supplementary European Search Report for European Patent Application No. EP 11154547.1, titled "Blunt Tip Obturator", dated Mar. 22, 2011.
European Patent Office, European Search Report for European Application No. 11191191.3, titled "Bladeless Obturator" dated Feb. 29, 2012.
European Patent Office, European Search Report for European Application No. 11191179.8, titled "Bladeless Obturator", dated Feb. 21, 2012.
European Patent Office, European Search Report for European Application No. 11191193.9, titled "Bladeless Obturator", dated Mar. 5, 2012.
European Patent Office, European Search Report for European Application No. 11191187.1, titled Bladeless Obturator, dated Feb. 23, 2012.
European Patent Office, European Search Report for European Application No. 11191184.8, titled "Bladeless Obturator", dated Feb. 23, 2012.
European Patent Office, European Search Report for European Application No. 11191189.7, titled "Bladeless Obturator", dated Feb. 24, 2012.
European Patent Office, European Search Report for European Application No. 11191175.6, titled "Bladeless Obturator", dated Feb. 21, 2012.
European Patent Office, European Search Report for European Application No. 047017314, titled "Surgical Access Apparatus and Method", dated Mar. 30, 2007.
Taut, Inc., ADAPT-Asymmetrical Dilating Access Port, Geneva Illinois.
Karl Storz, The Karl Storz Ternamian EndoTIP (TM) System, date: Aug. 27, 2001.
Karl Storz, Zerocart Trocar with eccentric tip, Recklinghausen, Germany, date Mar. 7, 2001.
Ethicon Endo-Surgery, Inc., ENDOPATH Minimally Invasive Access, date: 2001.
European Patent Office, Invitation to Pay Additional Fees for International Application No. PCT/US2012/036119, entitled "Low-Profile Surgical Universal Access Port", mailed Jul. 13, 2012.
European Patent Office, European Search Report for European Application No. 12187933, titled "Insufflating Optical Surgical Instrument", dated Nov. 20, 2012.
European Patent Office, European Search Report for European Application No. 12187929, titled "Insufflating Optical Surgical Instrument", dated Nov. 20, 2012.

\* cited by examiner

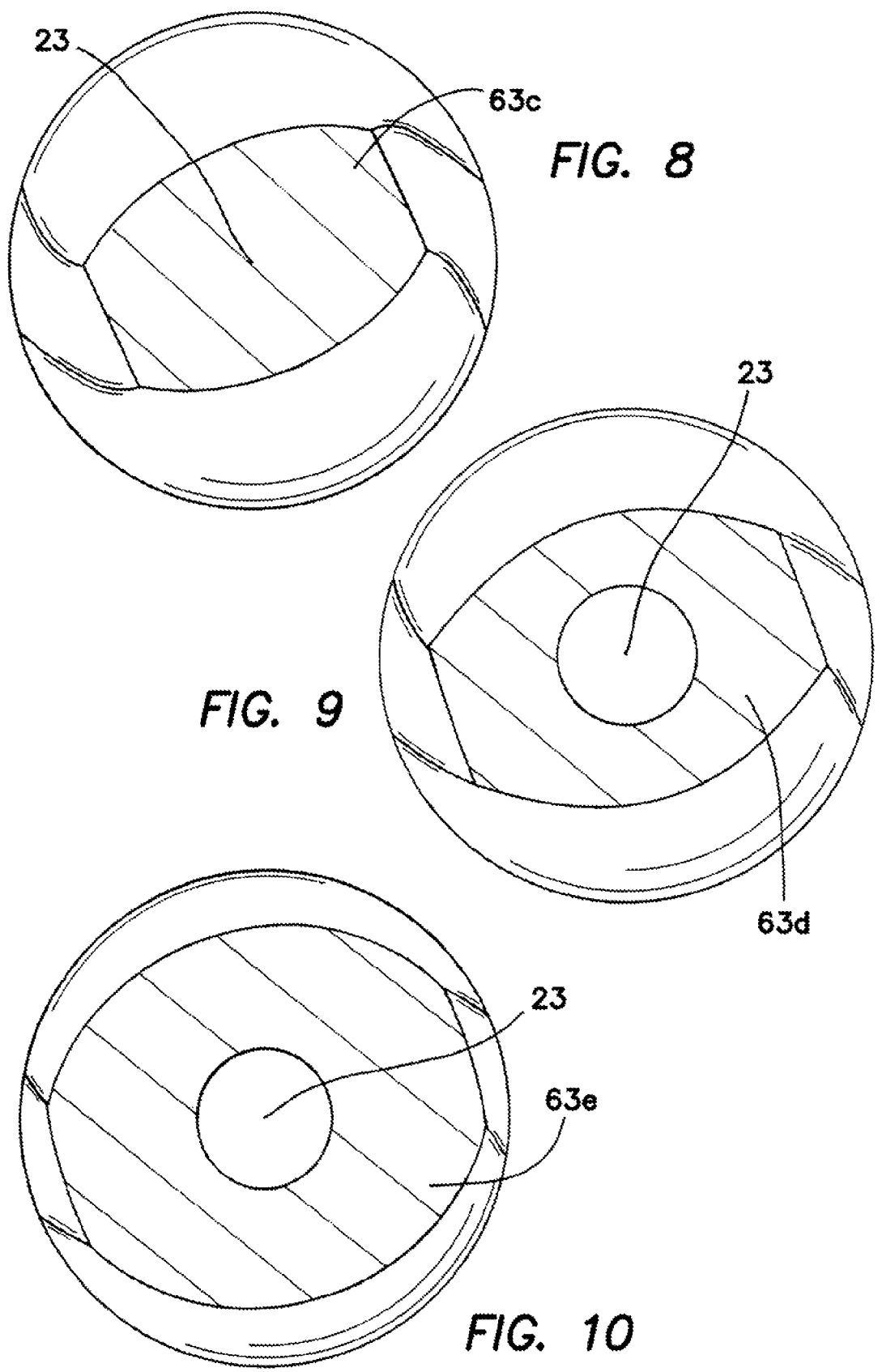

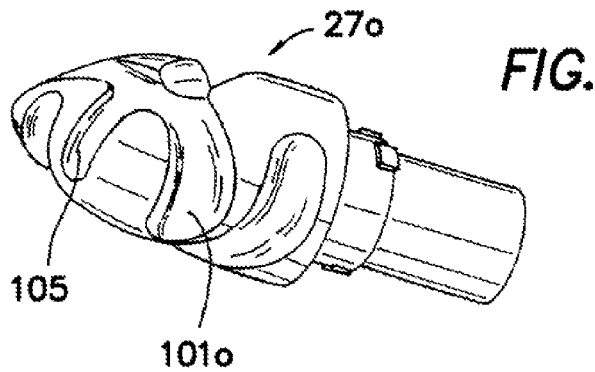
FIG. 26
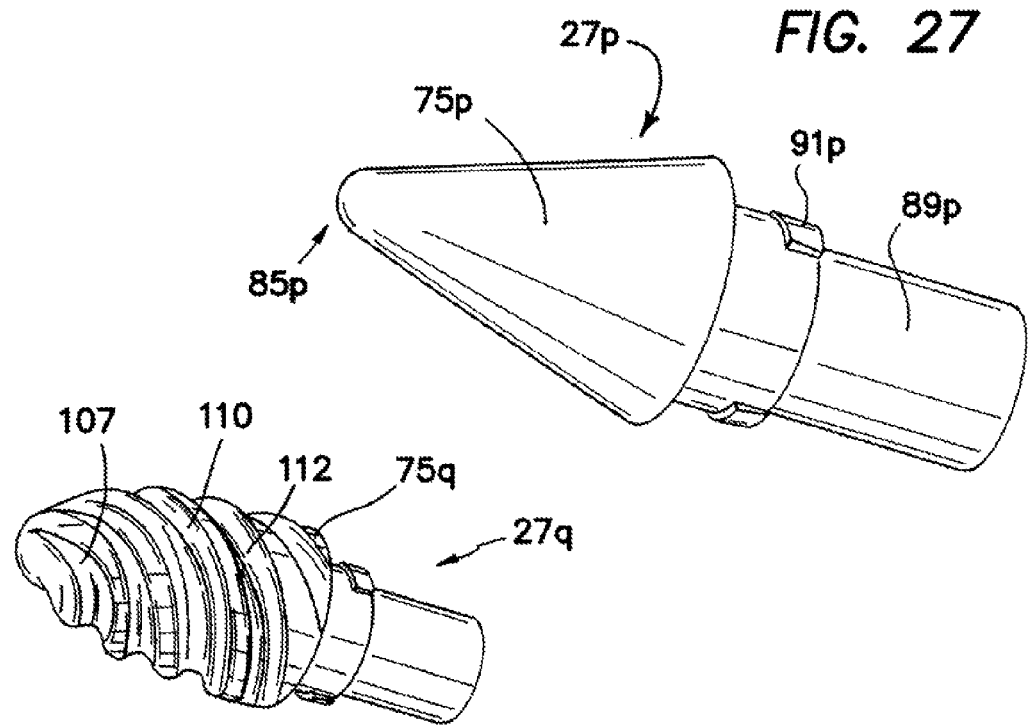
FIG. 27
FIG. 28
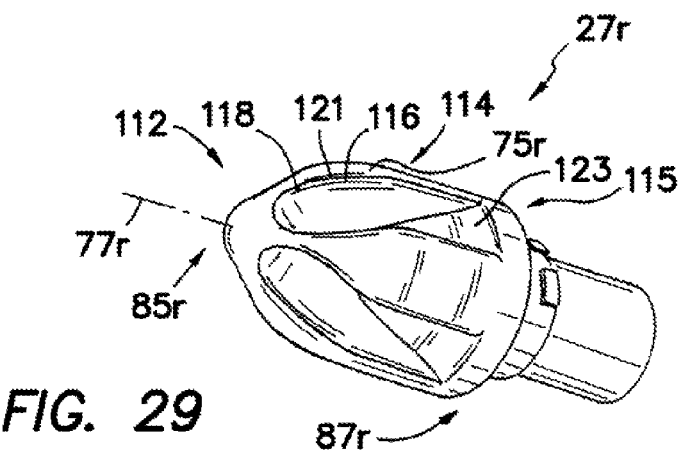
FIG. 29

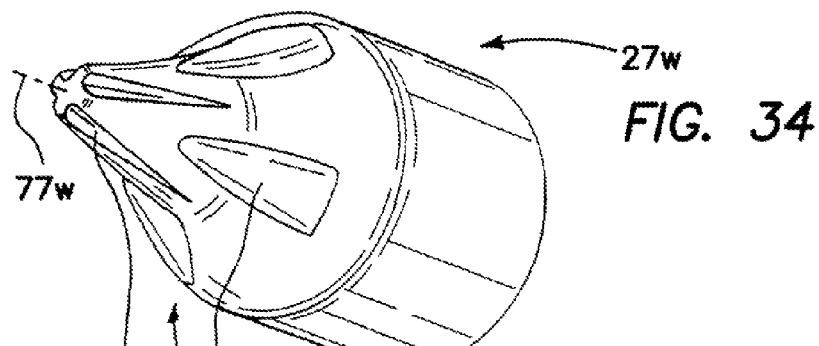
FIG. 34
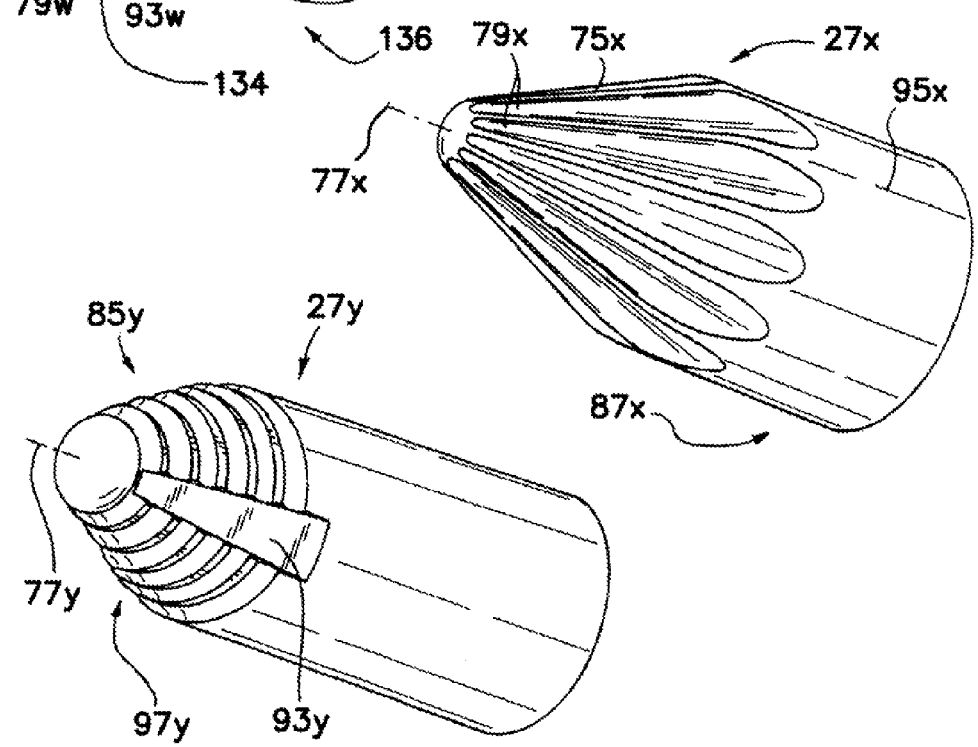
FIG. 35
FIG. 36
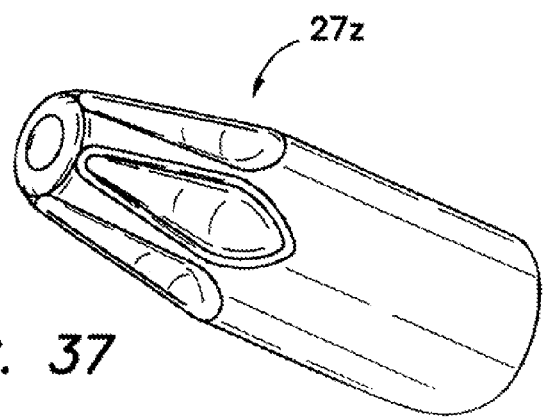
FIG. 37

BLADELESS OBTURATOR

CROSS REFERENCE TO RELATED APPLICATIONS

This application is a continuation of U.S. application Ser. No. 10/489,403, now U.S. Pat. No. 7,686,823, which entered the National Phase under 35 U.S.C. §171 on Mar. 11, 2004 from International Application No. PCT/US2002/06759, filed Mar. 4, 2002, which claims the benefit of U.S. Application No. 60/324,613, filed on Sep. 24, 2001, the entire disclosures of which are incorporated herein by reference.

FIELD OF THE INVENTION

This invention relates generally to trocar systems including obturators, and more specifically, bladeless obturators.

BACKGROUND

Trocar systems have been of particular advantage in facilitating less invasive surgery across a body wall and within a body cavity. This is particularly true in the case of the abdominal surgery where trocars have provided working channels across the abdominal wall to facilitate the use of instruments within the abdominal cavity. Particularly in this form of surgery, it is advantageous to insufflate, inflate, or pressurize the abdominal cavity in order to provide an increased working volume. In the interest of maintaining this insufflation, trocars have been provided with valves which form at least two seals: across the working channel a zero seal in the absence of an instrument, and an instrument seal in the presence of an instrument.

The trocar systems of the past typically includes a cannula, which defines the working channel, and an obturator which is used to place the cannula across the abdominal wall. The obturator is inserted into the working channel of the cannula and then pushed through the abdominal wall with a penetration force of sufficient magnitude to result in penetration of the abdominal wall. Once the cannula is in place, the obturator can be removed.

In the past, obturators have been developed with an intent to provide a reduction in the force required for penetration. Sharp blades have typically been used to enable the obturator to cut its way through the abdominal wall. While the blades have facilitated a reduced penetration force, they have been of particular concern once the abdominal wall has been penetrated. Within the abdominal cavity, there are organs which need to be protected against any puncture by an obturator.

In some cases, shields have been provided with the obturators in order to sense penetration of the abdominal wall and immediately shield the sharp blades. These shielding systems have been very complex, have required a large amount of time to deploy, and have generally been ineffective in protecting the organs against the sharp blades.

Blunt-tip obturators have been contemplated with both symmetrical and asymmetrical designs While the blunt tip tends to inhibit damage to interior organs, it also tends to increase the penetration force associated with the obturator.

In some cases, blunt tip obturators have been adjusted to take advantage of the known anatomy associated with the abdominal wall. This anatomy includes three layers of muscle, each layer having parallel fibers which extend in a particular direction that is different for each of the layers. Notwithstanding this knowledge of the anatomy, prior attempts to develop blunt-tip obturators have not taken full advantage of this anatomical structure.

SUMMARY

In accordance with the present invention, a blunt tip obturator is disclosed with characteristics which take farther advantage of the abdominal anatomy. In several embodiments, the obturator has a blunt tip with a blade configuration particularly adapted for alignment parallel to the fibers of the muscle layers. With a twisted configuration, this tip transitions through a rectangular cross section to a circular cross section as it twists radially from a distal end to a proximal end of the tip. This configuration facilitates insertion with a reduced penetration force as the user moves the tip back and forth radially while applying an axial penetration force. With the blade tip having a length to width ratio greater than one, the blade can be inserted between the fibers and then rotated to provide increased fiber separation and thereby facilitate accommodation of the larger diameter associated with the cannula.

In one aspect of the invention, a surgical obturator is adapted to penetrate a body wall. The obturator includes an elongate shaft extending along an axis between a proximal end and a distal end. A bladeless tip is disposed at the distal end of the shaft, the tip having an outer surface extending distally to a blunt point. The outer surface has a pair of side sections separated by an intermediate section. One of the side sections extends from the blunt point radially outwardly with progressive position proximally along the axis. This side section includes a distal portion in proximity to the blunt point and a proximal portion in proximity to the shaft. The distal portion of the one side section is twisted radially with respect to the proximal portion of the one side section The intermediate section extends across the blunt point of the bladeless tip.

In another aspect of the invention, a bladeless tip is disposed at the distal end of the shaft and has an outer surface with the distal portion and a proximal portion. The outer surface of the tip in radial cross section has the general configuration of a geometric shape with a side. The side of the geometric shape in the distal portion of the tip rotates in the first direction about the axis in progressive proximal radial cross sections along the axis. The side of the geometric shape in the proximal portion of the tip rotates in a second direction opposite to the first direction with progressive proximal radial cross sections along the axis.

In an additional aspect of the invention, the bladeless tip has an outer surface including a pair of generally opposed sections. The outer surface has a geometric shape in progressive radial cross sections from a distal cross section to a proximal cross section A pair of generally opposed sections of the outer surface appear as a pair of lines in each of the progressive radial cross sections, with at least one of the lines becoming increasingly arcuate in the progressive radial cross sections.

In a further aspect of the invention, the bladeless tip is coupled to the shaft and has an axis extending between a proximal end and a distal end, the tip having an outer surface with a generally conical configuration and a blunt tip. Portions of the outer surface define at least one recess extending relative to the axis generally between the proximal end and the distal end of the tip.

These and other features and advantageous of the invention will become more apparent with a discussion of preferred embodiments in reference to the associated drawings.

BRIEF DESCRIPTION OF THE DRAWINGS

FIG. 8 is a radial cross section view taken along lines 8-8 of FIG. 4;

FIG. 9 is a radial cross section view taken along lines 9-9 of FIG. 4;

FIG. 10 is a radial cross section view taken along lines 10-10 of FIG. 4;

FIG. 12-37 show perspective views of other embodiments of the blunt tip of the present invention.

DESCRIPTION OF PREFERRED EMBODIMENTS

Figure 1:
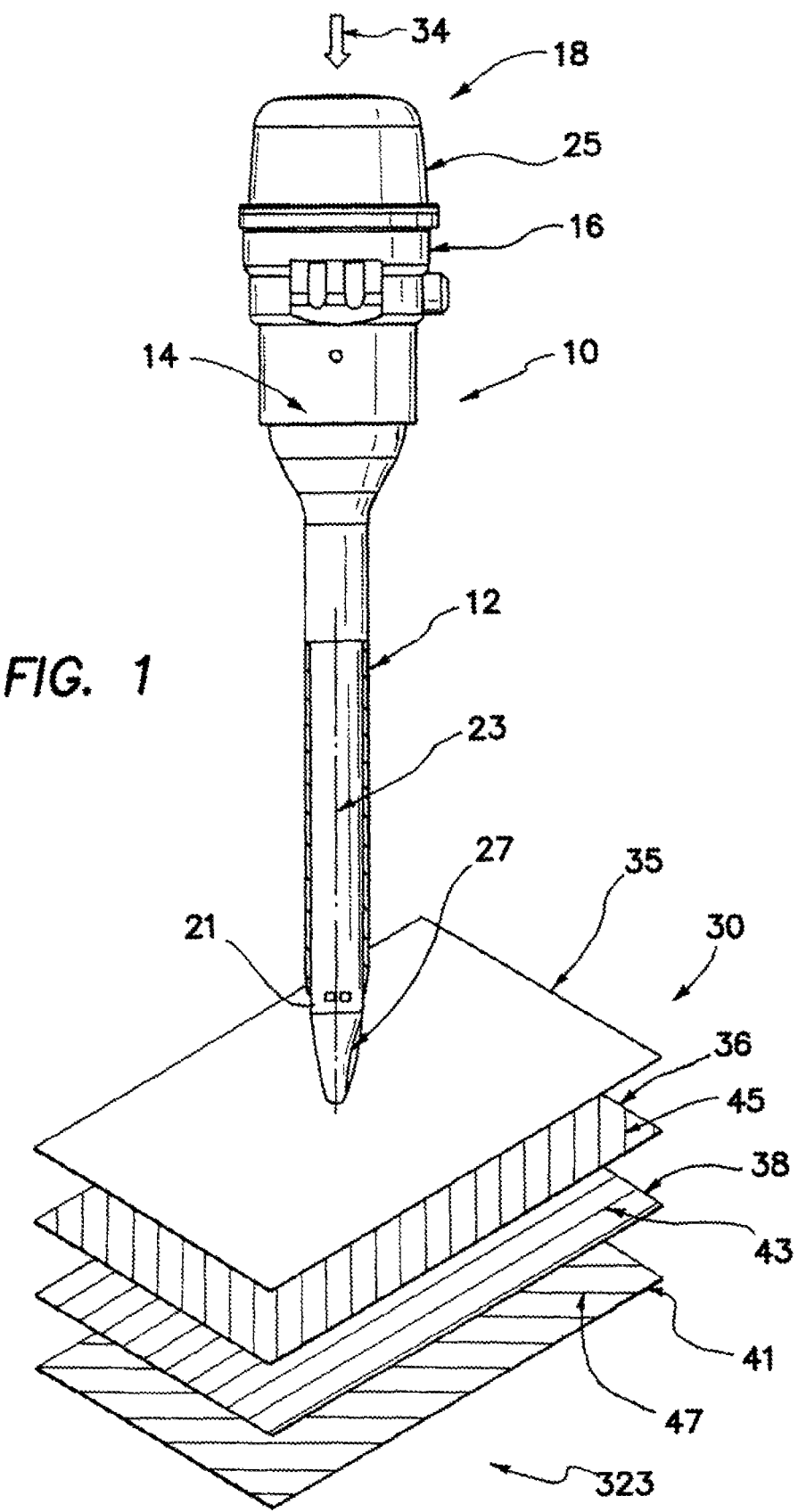
FIG. 1 is a side elevation view of a trocar system including a cannula with associated valve housing, and an obturator with a blunt tip extending through the working channel of the cannula to facilitate placement across the abdominal wall.

A trocar system is illustrated in FIG. 1 and designated by the reference numeral 10. This system includes a cannula 12, defining a working channel 14, and a valve housing 16. The system 10 also includes an obturator 18 having a shaft 21 extending along an axis 23. A handle 25 is disposed at a proximal end of the shaft at 21 while a blunt tip 27 is disposed at a distal end of the shaft 21. The shaft 21 of the obturator 18 is sized and configured for disposition within the working channel 14 of the cannula 12 With this disposition, illustrated in FIG. 1, the obturator functions to penetrate a body wall such as the abdominal wall 30 to provide the cannula with access across the wall 30 and into a body cavity, such as the peritoneal or abdominal cavity 32. The blunt tip 27, which initially facilitates penetration of the abdominal wall 30 can be removed with the obturator 18 once the cannula 12 is operatively disposed with the working channel 14 extending into the abdominal cavity 32.

In order to facilitate penetration of the abdominal wall 30 by the trocar system 10, a penetration force, represented by an arrow 34, is typically applied along the axis 23. It can be appreciated that the force required to penetrate the abdominal wall 30 drops significantly once the wall 30 is penetrated. Further application of the force 34, even for an instant of time, can result in injury to organs within the cavity 32. Where the obturators of the past have included blades facilitating penetration of the abdominal wall, these blades have been particularly threatening and detrimental to the interior organs.

Consequently, in accordance with the present invention, the tip 27 of the obturator 18 is provided with a blunt configuration. As noted, blunt tips have been used in the past to significantly reduce any potential for damage to interior organs. Unfortunately, these blunt tips have increased significantly the amount of force 34 required for penetration of the abdominal wall 30.

The blunt tip 27 of the present invention takes into account an anatomical configuration of the abdominal wall 30 with an improved structural design and method of insertion.

In order to fully appreciate the aspects of this invention, it is helpful to initially discuss the anatomy associated with the abdominal wall 30. This wall 30 typically includes the skin or fascia 35 and a series of muscles in the form of muscle layers 36, 38 and 41 These layers are each defined by muscle fibers which extend generally parallel to each other in a direction which is different for each of the layers. For example, the layer 38 is composed of fibers 43 which extend generally parallel in a particular direction. Fibers 45 associated with the layer 36 extend generally parallel at an angle such as 45 degrees to the particular direction of the fibers 43 Fibers 47 associated with the layer 41 also extend in a parallel direction but at an angle of about 45 degrees to the fibers 43 and an angle of about 90 degrees to the fibers 45.

Having noted the directional nature of the fibers, such as the fibers 45, it can be appreciated that such a structure is most easily penetrated by a tip 27 having a narrow width which is capable of being moved generally parallel to and between the fibers associated with a particular muscle layer. This narrow width might be provided with a point configuration or in the case of a preferred embodiment, a line or rectangular configuration having the narrow width and a longer length. With the length oriented parallel to the fibers of a particular laser a reduced penetration force 34 is required to push the obturator 18 through the particular layer.

Unfortunately, with the fibers 45, 43 and 47 oriented at 45 degrees to each other, proper alignment of the tip 27 for penetration of one layer, such as the layer 36, will not necessarily result in proper alignment for penetration of the next layer, such as the layer 38. For this reason, the rectangular configuration for the tip 27 is twisted slightly so that penetration of the first layer 36 begins to rotate the distal end of the tip 27 into proper orientation for penetration of the next layer 38

The twisted configuration of the tip 27 also causes the tip 27 to function with the mechanical advantage of a screw thread. With this configuration, a preferred method of placement requires that the user grip the handle 25 of the obturator 18, and twist it about the axis 27. This twisting motion in combination with the screw configuration of the tip 27 converts radial movement into forward movement along the axis 23. Thus, the user applies both a forwardly directed force as well as a radial force to move the trocar system 10 in a forward direction. Since all of the force supplied by the user is not directed axially along the arrow 34, this concept avoids the tendency of prior trocar systems to jump forward upon penetration of the wall 30.

Figure 2:
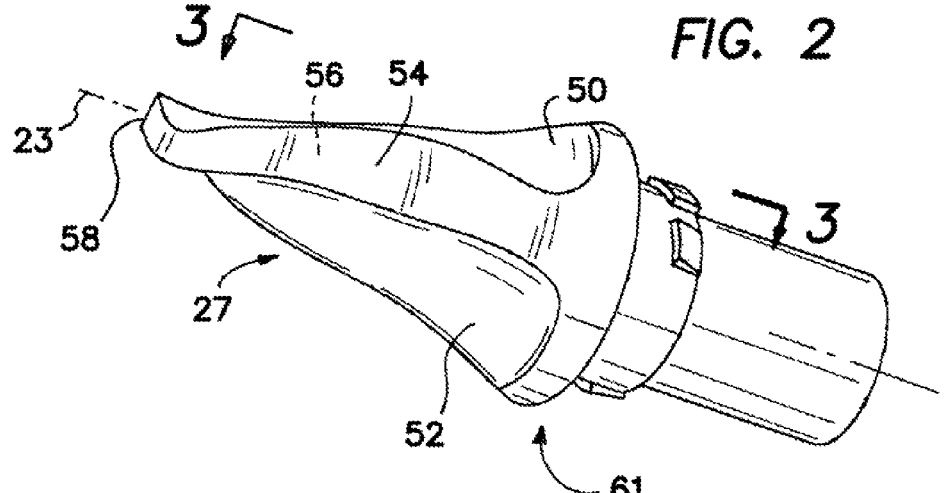
FIG. 2 is a perspective view of a preferred embodiment of the blunt tip illustrated in FIG. 1.
Figure 3:
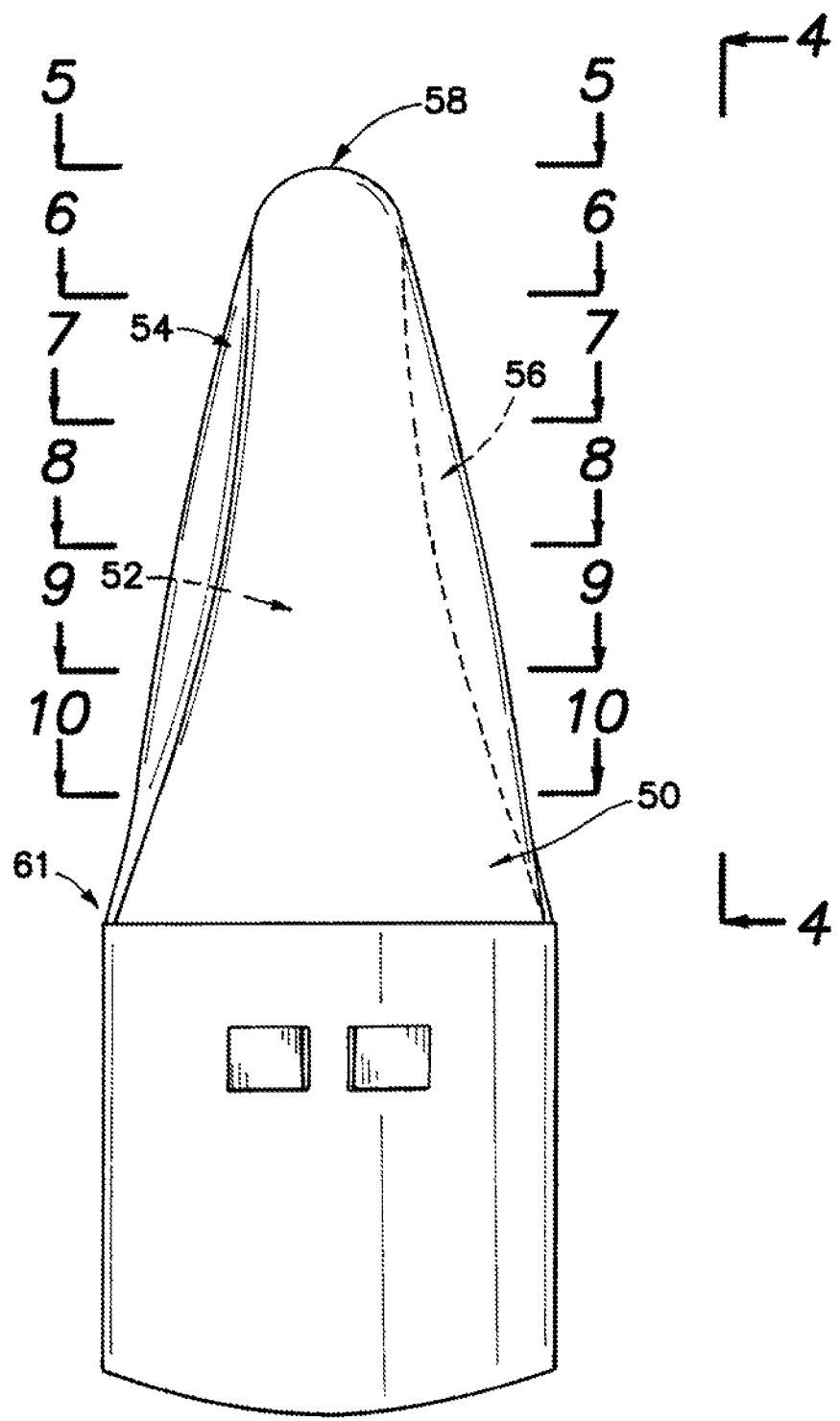
FIG. 3 is a side elevation view of the blunt tip taken along lines 3-3 of FIG. 2.
Figure 4:
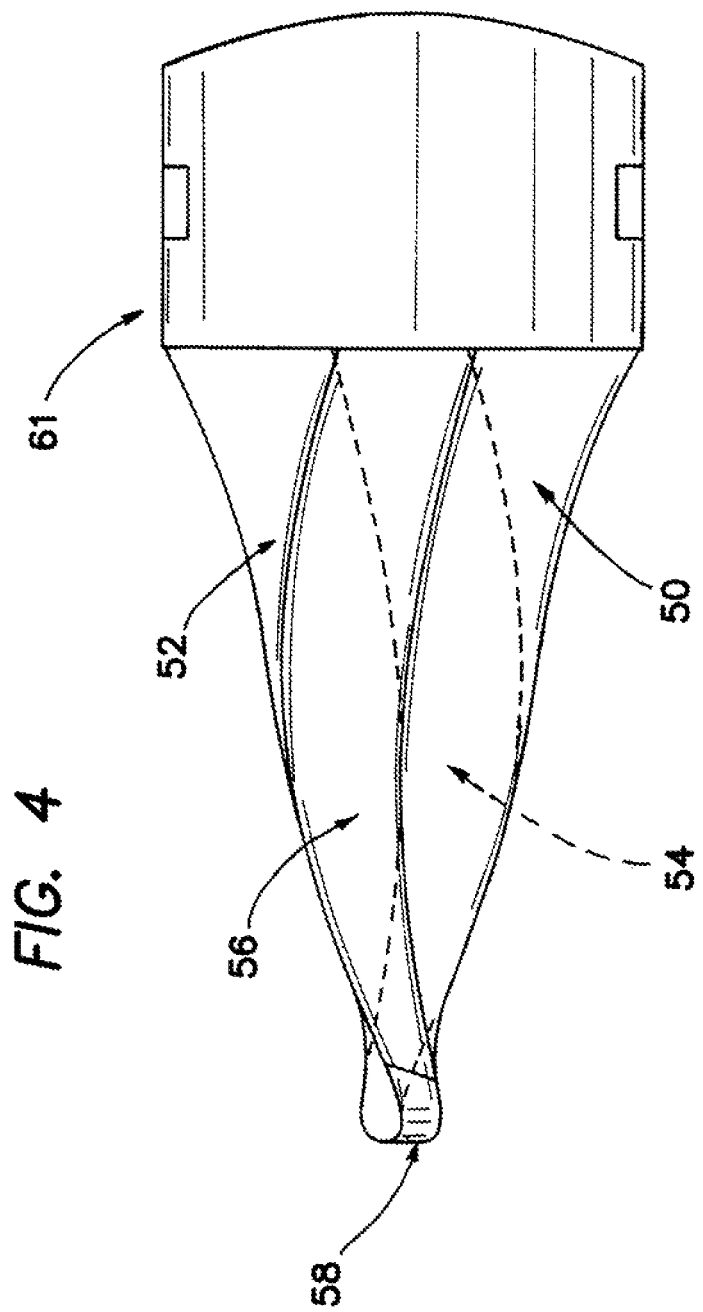
FIG. 4 is a side elevation view taken along lines 4-4 of FIG. 3.

The twisted and rectangular configuration of the tip 27 is most apparent in the schematic view of FIG. 2 and the side elevation views of FIGS. 3 and 4. In this embodiment, the tip is composed generally of four surfaces: two opposing major surfaces 50 and 52, separated by two side surfaces 54 and 56 which extend between an end surface 58 and a proximal base 61. A plane drawn through the axis 23 would show the tip 27 in this case, to be composed of two symmetrical halves.

Figure 5:
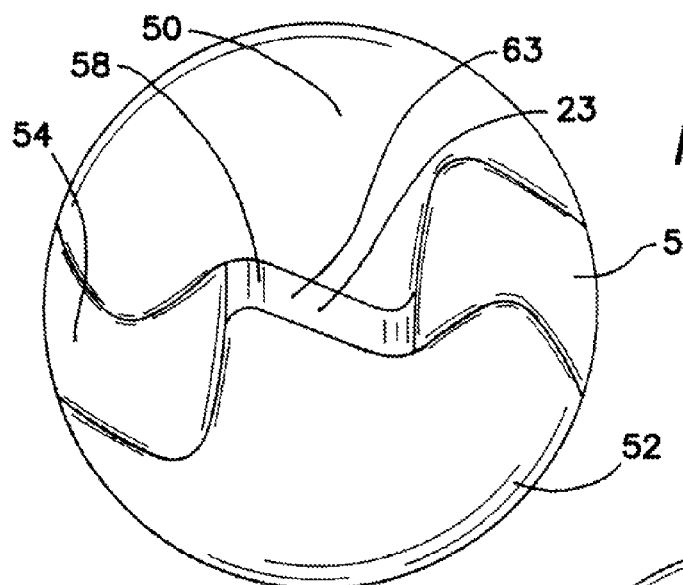
FIG. 5 is an end view taken along lines 5-5 of FIG. 4.
Figure 6:
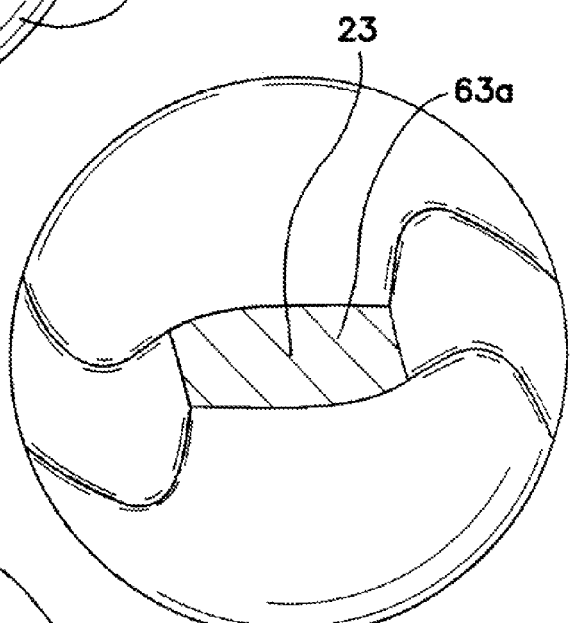
FIG. 6 is a radial cross-section view taken along line 6-6 of FIG. 4.
Figure 7:
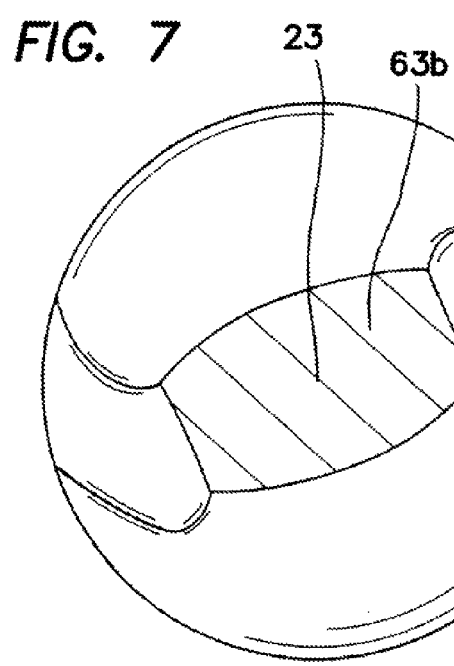
FIG. 7 is a radial cross-section view taken along line 7-7 of FIG. 4.

The major surfaces 50 and 52 and the side surfaces 54 and 56 generally define the cross section of the tip 27 to be rectangular from the distal surface 58 to the proximal end 61. This configuration can best be appreciated with reference to the cross section views of FIGS. 5-10. In FIG. 5, the distal end of the tip 27 is shown with a rectangle having the greatest length to width ratio. This rectangle, designated by the reference numeral 63, also has a twisted, S-shaped configuration at the distal-most end of the tip 27.

As views are taken along progressive proximal cross sections, it can be seen that the rectangle 63 becomes less twisted, and the width increases relative to the length of the rectangle 63. The spiral nature of the tip 27 is also apparent as the rectangle moves counterclockwise around the axis 23 in the embodiment of FIG. 2. This is perhaps best appreciated in a comparison of the rectangle 63 in FIG. 7 relative to that in FIG. 6. With progressive proximal positions, the rectangle 63 begins to fatten with a reduction in the ratio of length to width. The long sides of the rectangle 63 also tend to become more arcuate as they approach a circular configuration most apparent in FIGS. 9 and 10. In these figures, it will also be apparent that the rotation of the rectangle 63 reaches a most counterclockwise position and then begins to move clockwise. This is best illustrated in FIGS. 8, 9 and 10. This rotation back and forth results from the configuration of the side surfaces 54 and 56, which in general, have a U-shape best illustrated in FIGS. 2 and 3.

The ratio of the length-to-width of the rectangle 63 is dependent on the configuration of the side surfaces 54 and 56, which defined the short sides of the rectangle 63 as well as the configuration of the major surfaces 50 and 52 which define the long sides of the rectangle 63. Again with reference to FIG. 3, it can be seen that the side surfaces 50 and 52 are most narrow at the distal end of the tip 27. As these surfaces extend proximally, they reach a maximum width near the point of the most counterclockwise rotation, shown generally in FIG. 8, and then reduce in width as they approach the proximal end 61. Along this same distal to proximal path, the major surfaces 50 and 52 transition from a generally flat configuration at the distal end to a generally conical configuration at the proximal end 61.

Figure 11:
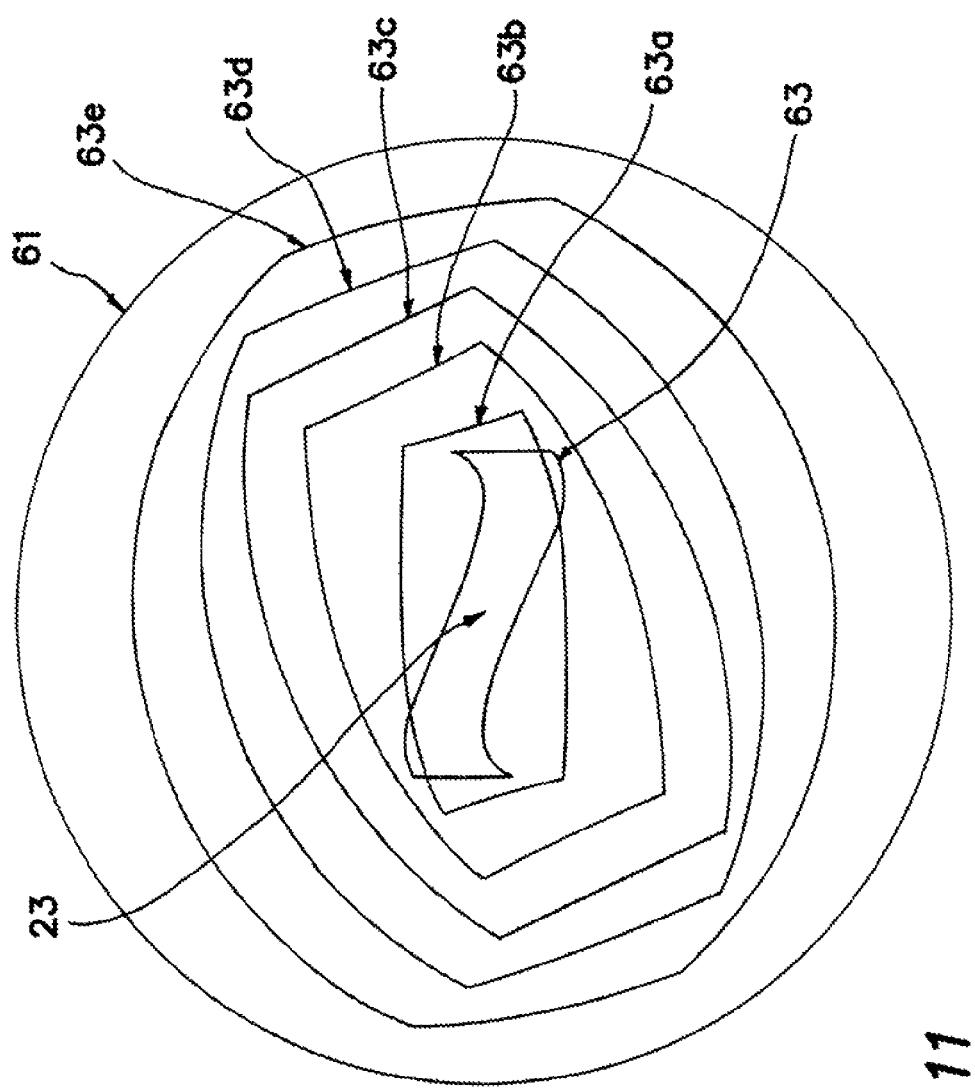
FIG. 11 is a schematic view illustrating each of the figures of 5-10 super-imposed to facilitate an understanding of the twisted configuration of the blunt tip.

In the progressive views of FIGS. 6-10, the rectangle 63 is further designated with a lower case letter a, b, c, d, or e, respectively. In FIG. 11, the rectangles 63 and 63a-63c are superimposed on the axis 23 to show their relative sizes, shapes, and angular orientations A preferred method of operating the trocar system 10 benefits significantly from this preferred shape of the blunt tip 27. With a rectangular configuration at the distal surface 58, the end of the tip 27 appears much like a flathead screwdriver. The length of the surface 58 is aligned parallel with the fibers 45 of the layer 36. With this shape, the simple back and forth twisting motion tends to separate the fibers 45 along natural lines of separation, opening the muscle layer 36 to accept the larger diameter of the cannula 12. By the time the first layer 36 is substantially penetrated, the twisted configuration of the blunt tip 27 turns the rectangle at the distal surface 58 more into a parallel alignment with fibers 43 in the next layer 48. Again, a twisting or dithering motion facilitates an easy separation of these fibers requiring a significantly reduced penetration three along the arrow 34.

When the muscle layer 38 is sufficiently penetrated, the twisted configuration of the tip 27 automatically rotates the rectangular end surface 58 into generally parallel alignment with the fibers 47 of the next layer 41. Again, the natural separation of these fibers 47 together with the unique configuration of the tip 27, accommodates the further penetration of the layer 41 until the cannula 12 is operatively disposed across the wall 30. It will be noted in particular that the fibers 45, 43, and 47 are naturally separated, not cut. This has two advantageous effects: 1) the abdominal wall 30 easily closes upon removal of the trocar system 10; and 2) without cutting, very little bleeding is encountered and very little healing is required to seal the wound permanently.

Certainly, one of the primary purposes of the invention is to maintain control and facilitate entry into the body cavity 32 while inhibiting any tearing or cutting of tissue. The tip 27 is bladeless, blunt, and atraumatic to organs and bowel within the peritoneal or abdominal cavity 32. The tip 27 also minimizes tenting of the peritoneum and allows for a safe entry. The device is used in conjunction with the cannula 12 to create an initial entry way into the peritoneal cavity 32. The obturator is first inserted through the valve housing 16 and into the cannula 12. The entire trocar system 10 is then inserted through the abdominal wall 30 and into the peritoneal cavity 32. Once the cannula 12 is properly placed, the obturator 18 can be removed.

This facilitates a unique method of separating tissue and could apply to any object with a slim profile and flat sides When inserted into the peritoneum the slim profile of the device requires very little area to move safely between tissue and muscle fibers. The device can then be rotated in alternating clockwise and counterclockwise directions while the downward penetration force is applied. When rotated in alternating directions, the tissue is moved apart and a larger opening is created for a profile of greater cross sectional area to follow. This process continues with safety and easy until the device enters the peritoneal cavity 32 and moves to its operative position.

When the cannula 12 is ultimately removed, the size of the opening left in the tissue is minimal. Importantly, this opening is left sealed due to a dilating effect caused by the mere separation of fibers. Note that there are no blades or sharp edges to cut muscle fiber, and thereby prolong the healing process.

In other embodiments, the tip 27 of the obturator can be fabricated of a translucent or clear material, and the handle provided with a passageway along the inside of the tip. With this configuration, a laparoscope can be inserted through the handle of the obturator and through the shaft to the tip Insertion can then be monitored through the laparoscope, and the clear tip of the obturator, in order to further ensure safe entry.

The obturator 18 can be constructed as a single component or divided into two components such as the shaft 21 and the tip 27. If the obturator 18 is constructed as a single component, it may be constructed of either disposable or reusable materials. If the obturator 18 is constructed as two or more components, each component can be made either disposable or useable as desired for a particular configuration In a preferred embodiment, the obturator shaft 21 and handle are made of a reusable material, such as a metal or an autoclavable polymer in order to facilitate re-sterilization and reuse of these components. In this embodiment, the tip 27 is made of a material that is not autoclavable and therefore is adapted to be disposable.

The blunt tip 27 can be coated or otherwise constructed from a soft elastomeric material. In such a case, the material could be a solid elastomer or composite elastomer/polymer.

The obturator could also contain a spring-biased shield to cover the tip. On entry the shield could be retracted exposing the tip and then immediately and automatically moved distally back over the tip upon full entry into the peritoneal cavity 32. The action of the shield could also serve as an indicator to the surgeon that safe entry had been achieved. The obturator could be constructed in a manner wherein the tip 27 itself is spring biased and keyed to the shaft. The tip 27 would retract during insertion but would then deploy upon entry into the peritoneal cavity 32. This deployment action could also further serve as an indicator of safe entry.

The shaft 21 of the obturator 18 could be partially or fully flexible. With this configuration, the obturator 18 could be inserted through a passageway containing one or more curves of virtually any shape. A partially or fully flexed obturator 18 could then be used with a flexible cannula 12 allowing greater access to an associated body cavity 32.

The obturator 18 could also be used as an insufflation needle and provided with a passageway and valve to administer carbon dioxide or other insufflation gas to the peritoneal cavity 32. The obturator 18 could also be used with an insufflation needle cannula, in which cases removal of the obturator 18 upon entry would allow for rapid insufflation of the peritoneal cavity 32

The obturator 18 could also be constructed to permit free spinning of the tip about the axis 23. This would allow the tip 27 to find its own way through the abdominal wall 30 rather than relying on the user for clockwise and counterclockwise rotation.

Other embodiments of the invention are illustrated in FIG. 12-38 where elements of structure similar to those previously disclosed are designated with the same reference numeral followed by the lower case letters "a" to "z", respectively. Thus, in FIG. 12, the tip 27 is referred to with the reference numeral 27a while in FIG. 38, the tip is referred to with a reference numeral 27z.

Figure 12:
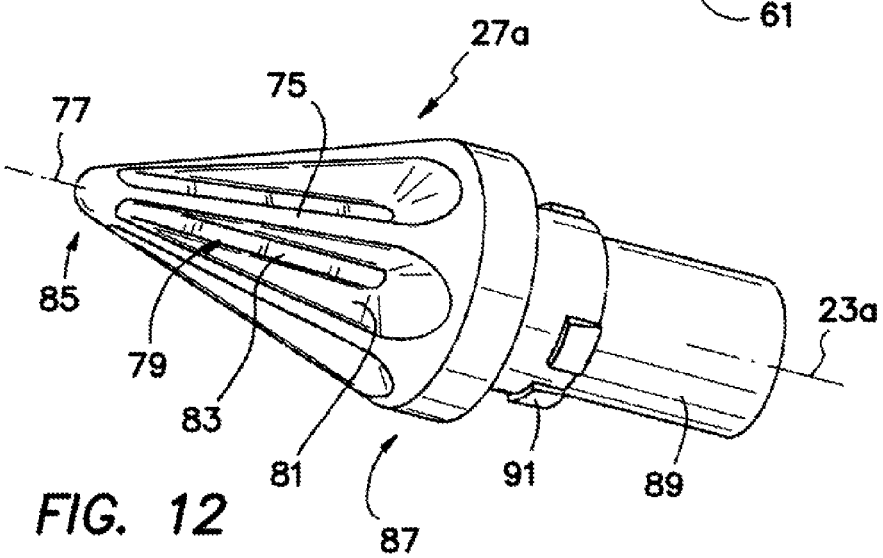

In FIG. 12, the obturator tip 27a is formed with a conical surface 75 having an axis 77. In this embodiment, the axis 77 of the surface 75 is collinear with the axis 23a of the tip 27a. A plurality of recesses 79 are formed in the conical surface 75 around the axis 77. These recesses are formed with side walls 81 which extend radially inwardly to a valley 83. In this embodiment, the conical surface 75 has an angle with respect to the axis 77 which is greater than an angle between the valley 83 and the axis 77. As a result, the recesses 79 appear to deepen relative to the surface 75 from a distal end 85 to a proximal end 87 of the tip 27a. The sidewalls 81 have a generally constant angle with respect to the conical surface 75 and consequently have an increased area toward the proximal end 87 The valley 83 has a generally constant width as it extends towards the proximal end 87.

In this embodiment, the tip 27a also has a cylindrical mounting shaft 89 with mounting lugs 91. This mounting shaft 89 is adapted to closely fit within the obturator shaft 21 (FIG. 1). The mounting lugs 91 can engage holes or shoulders within the shaft 21 to facilitate a fixed but removable relationship between the shaft 21 and tip 27a.

Figure 13:
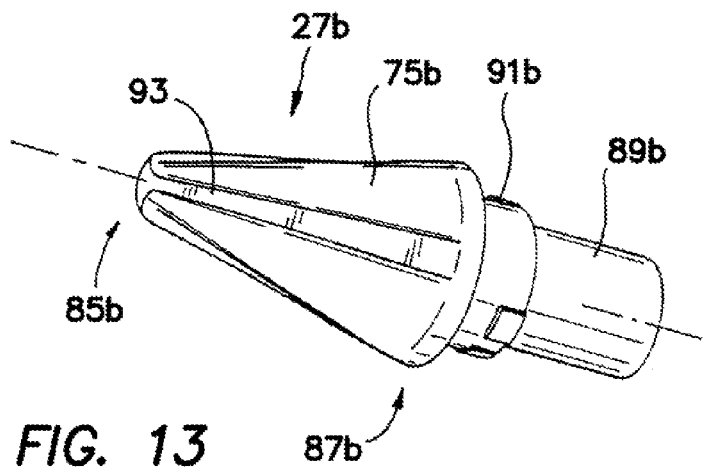

In FIG. 13, the tip 27b is also characterized by the conical surface 75b, the cylindrical mounting stub 89 and the lugs 91b. In this case, the tip 27b is provided with ridges 93 which extend radially outwardly from the conical surface 75b. The ridges 93 can have a constant width or a width which increases proximally as in the illustrated embodiment. The height of the ridges above the conical surface 75b can be either constant or variable between the distal end 85b and the proximal end 87b.

Figure 14:
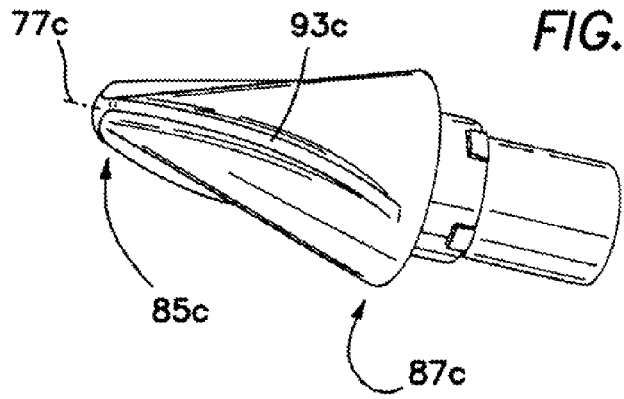

The obturator tip 27c in FIG. 14 is similar to that of FIG. 13 except that the ridges 93c are not straight but rather curved as they extend between the distal end 85c and the proximal end 87c. In this case, the ridges have an angle with respect to the axis 77c which increases proximally both radially and axially.

Figure 15:
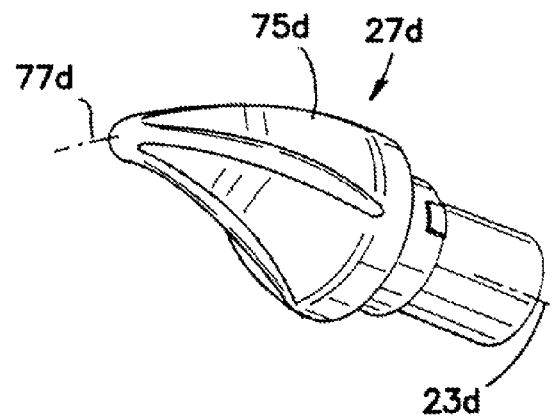

The obturator tip 27d in FIG. 15 is similar to that of FIG. 12 except that the axis 77d of the conical surface 75d is curved rather than straight. Accordingly, the axis 77d of the conical surface 75d is curved relative to the axis 23d of the obturator shaft 21d.

Figure 16:
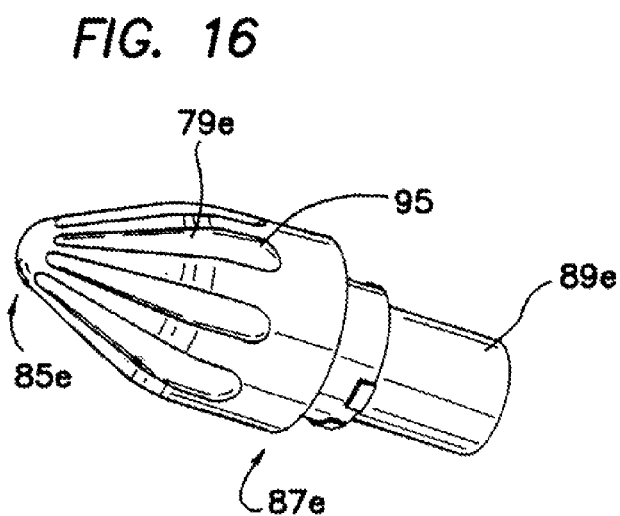

The obturator tip 27e in FIG. 16 is similar to that of FIG. 12 in that it includes the recess 79e which extend from the distal end 85e to the proximal end 87e. In this case however, the tip 27e has a cylindrical surface 95 which extends proximally of the conical surface 75e between the distal tip 85e and the mounting stub 89e. The recesses 79e in this embodiment extend along both the conical surface 75e and the cylindrical surface 95.

Figure 17:
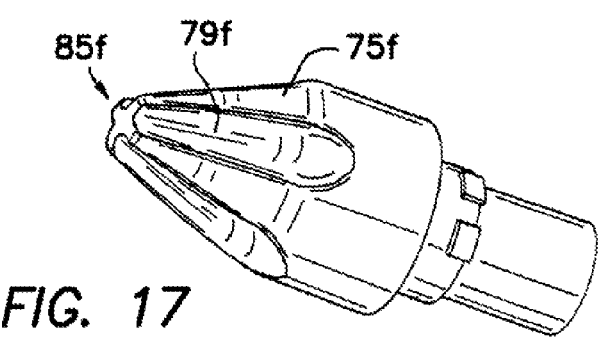

The obturator tip 27f of FIG. 17 is similar to that of FIG. 16 except that the recesses 79f extend through the distal end 85f In the illustrated embodiment, four of the recesses 79f provide the distal end 85f with the shape of the letter "X."

Figure 18:
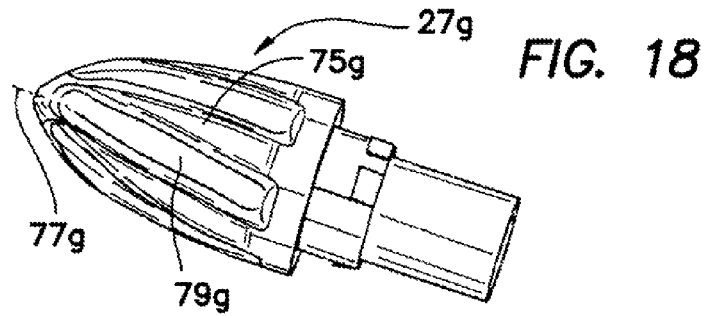

The obturator tip 27g in FIG. 18 is similar to that of FIG. 12 except that the surface 75g is more rounded thereby providing the tip 27g with a parabolic or bullet shape. Also, the recesses 79g are disposed at an angle with respect to any plane passing through the axis 77g.

Figure 19:
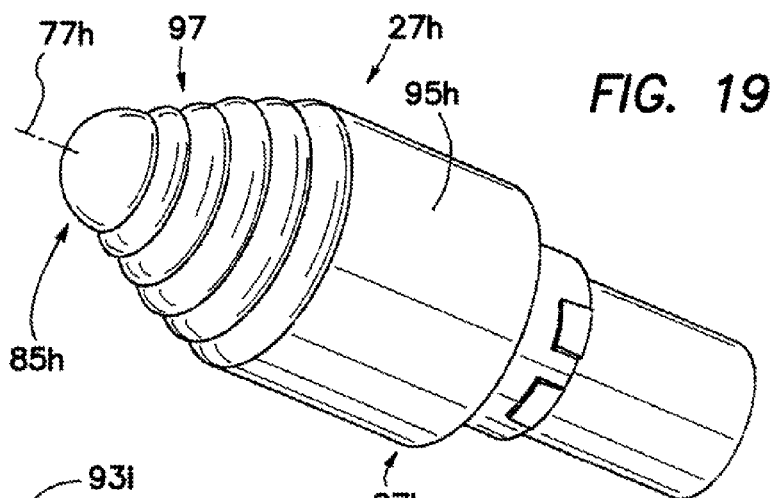

The obturator tip 27h in FIG. 19 has the cylindrical surface 95h at its proximal end 87h and a series of grooves 97 which extend circumferentially of the axis 77h with diameters which increase from the distal end 85h to the cylindrical surface 95h. Each of the recesses or ridges in the series 97h is disposed in an associated plane that is perpendicular to the axis 77h.

Figure 20:
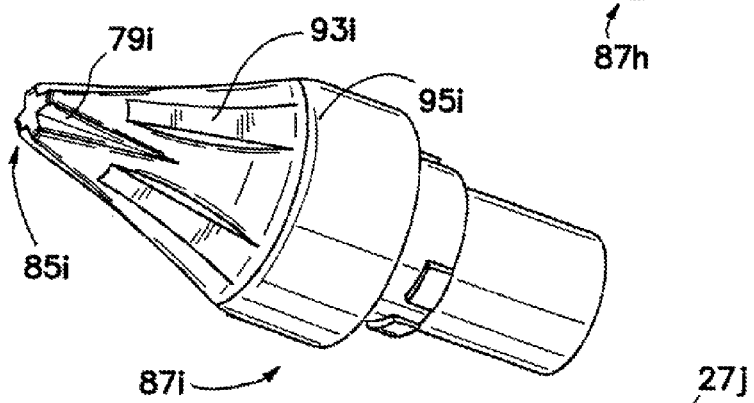

In the embodiment of FIG. 20, the tip 27i includes recesses 79i which are similar to those illustrated in FIG. 17 in that they extend through the distal end 85i. This embodiment also includes the ridges 93i which are disposed between the recesses 79i and extend toward the cylindrical surface 95i at the proximal end 87i. The recesses 79i in FIG. 20 have individual widths which decrease proximally.

Figure 21:
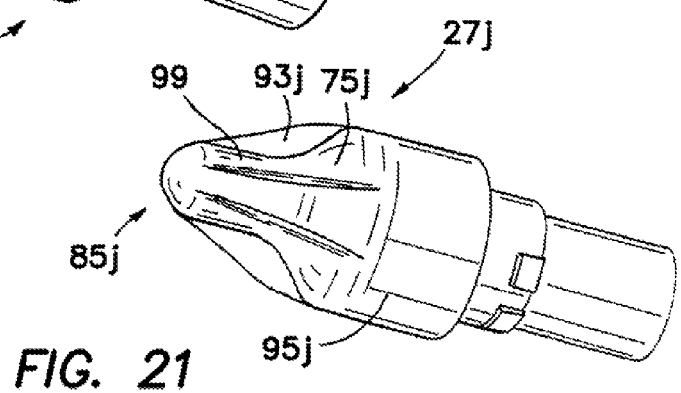

In the embodiment of FIG. 21, the tip 27j includes the conical surface 75j which transitions proximally into the cylindrical surface 95j. Distally of the conical surface 75j a second cylindrical surface 99j is provided which extends to the distal end 85j. Ridges 93j extend radially outwardly from the second surface 99 and the conical surface 75j.

Figure 22:
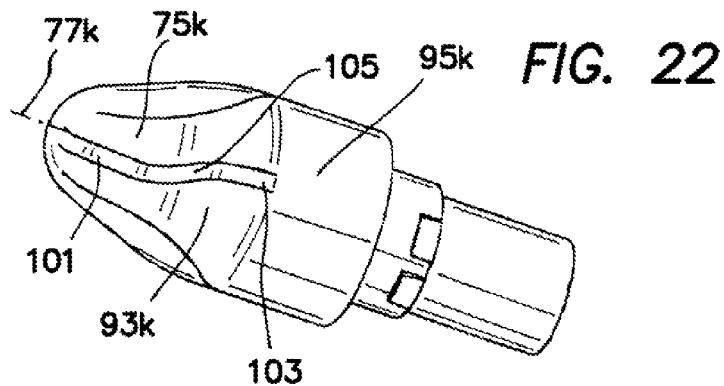

The obturator tip 27k in FIG. 22 is similar to previous embodiments having the conical surface 75k and the cylindrical surface 95k. In this embodiment, the ridges 93k include distally portions 101 and proximal portions 103 which extend in planes passing through the axis 77k. Between the proximal portions 103 and distal portions 101, the ridges 93k include intermediate portions 105 which extend in planes that do not include the axis 77k.

Figure 23:
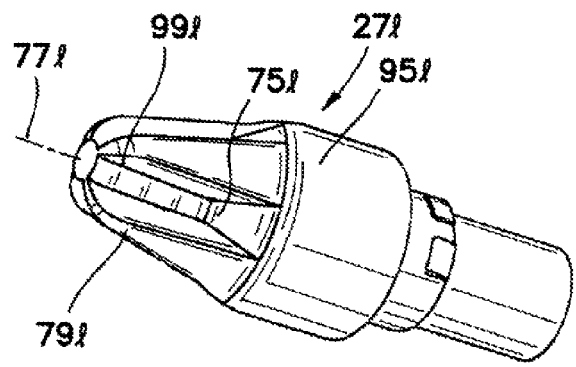

In FIG. 23, the tip 27l is similar to that of FIG. 17 except that the second cylindrical surface 99l is provided in this embodiment The recesses 79l have a generally constant width along the second cylindrical surface 99l and the conical surface 75l. These recesses 79l to not extend into the cylindrical surface 95l.

Figure 24:
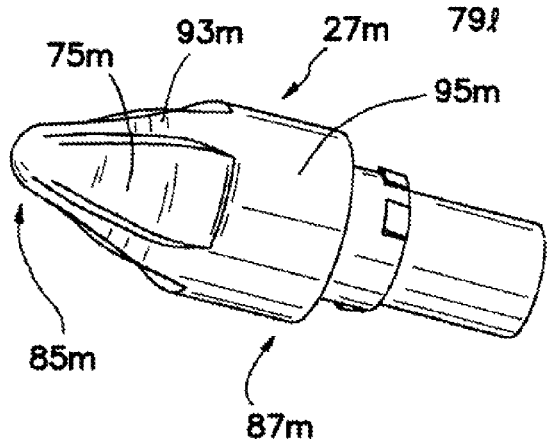

The obturator tip 27m in FIG. 24 is similar to that of FIG. 21 except that it does not include the second cylindrical surface 99m. In this case, the conical surface 75m extends to the distal end 85m with a slightly concave shape. The ridges 93m transition into the surface 75m at the distal end 85m and transition into the cylindrical surface 95m at the proximal end 87m. Between these two ends, the ridges 93m have a height which is increased by the concave configuration of the surface 75m.

Figure 25:
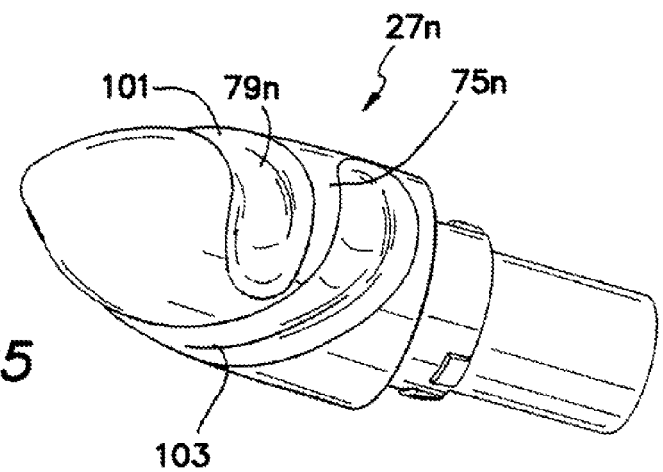

The tip 27n in FIG. 25 is similar to the tip 27g in FIG. 18 in that the outer surface 75n has a generally bullet-shaped configuration. The recesses 79n include a recess 101 which curves proximally in a counterclockwise direction, and a recess 103 which curves proximally in a clockwise direction.

The tip 27o in FIG. 26 is similar to that of FIG. 25 but includes a further recess 105 which spirals toward the distal end 85o in a clockwise direction. This spiral recess 105 crosses the recess 101o in this embodiment.

In FIG. 27, the tip 27p includes the conical surface 75p which extends toward the distal end 85p at its apex. The apex of the conical surface 75p is blunted at the distal end 85p. This embodiment also includes the mounting stub 89p and associated lugs 91p.

The tip 27q in FIG. 28 has the outer surface 75q with a bullet-shaped configuration. The recesses 79q in this embodiment include three recesses, 107, 110, and 112 which spiral in a generally parallel relationship proximally in a counter-clockwise direction.

The tip 27r in FIG. 29 has an outer surface 75r with a bullet-shaped configuration, and a plurality of recesses 79r which extend generally axially from the distal end 85 as to the proximal end 87r The recesses 79r are generally symmetrical and include a distal portion 114 with sidewalls 116 and 118 which define a deep valley 121 that extends generally parallel to the axis 27r. The proximal portion 115 of the recess 112 comprises a plane 123 which extends between the sidewalls 118 and 121 from the valley 116 radially outwardly with progressive positions toward the proximal end 87r.

Figure 30:
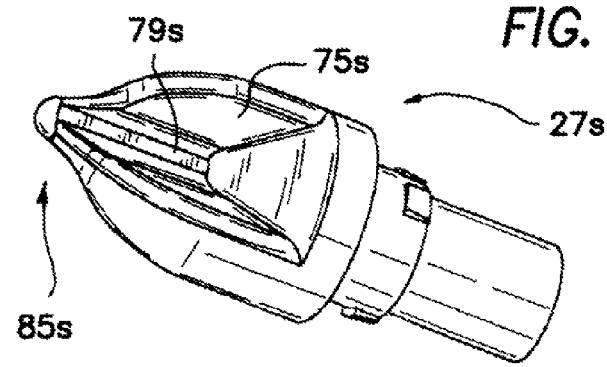

The tip 27s in FIG. 30 is similar to that of FIG. 29, but includes fewer recesses 79s. Also, the tip 27s has a nose that is more pointed thereby providing the outer surface 75s with a concave configuration near the distal end 85s.

Figure 31:
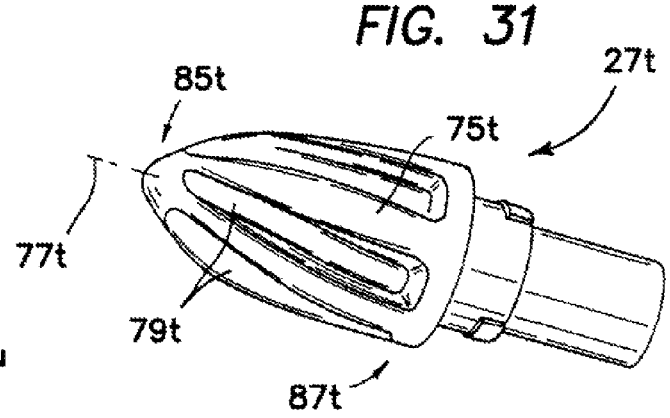

FIG. 31 shows a perspective view of the tip 27t with a bullet-shaped outer surface 75t and a plurality of the recesses 79t. In this case the recesses are straight but nevertheless have an angular relationship with the axis 77t. These recesses 79t extend through the distal end 85t but stop short of the proximal end 87t.

Figure 32:
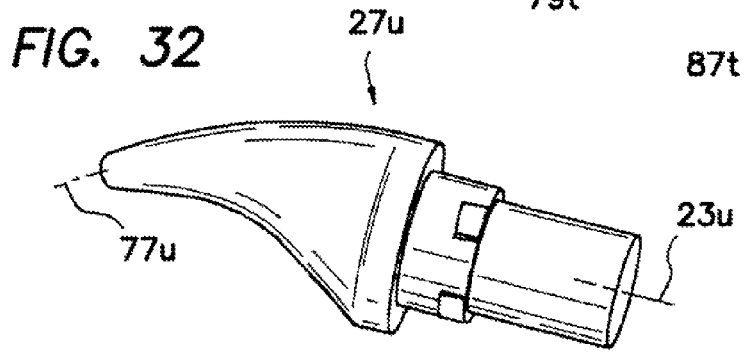

The tip 27u in FIG. 32 is similar to that of FIG. 15 in that the axis 77u is curved relative to the axis 23u which is straight. Also, in this embodiment, there are no ridges or recesses.

Figure 33:
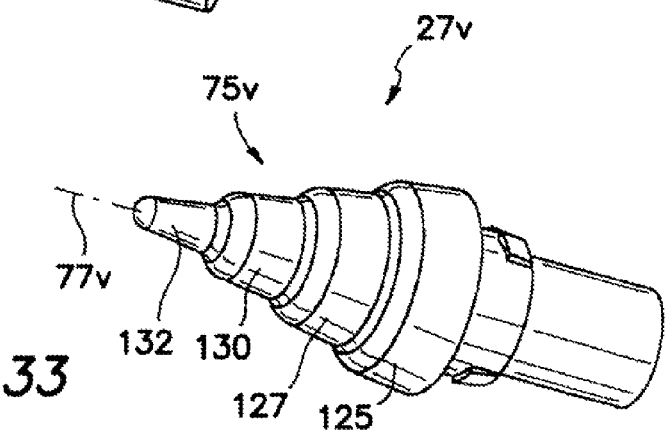

In FIG. 33, the tip 27v has an outer surface 75v which is formed by individual conical portions 125, 127, 130, and 132, which have progressively smaller average diameters. These conical portions 125-132 appear to be stacked with their individual axes disposed along the common axis 77v.

The tip 27w in FIG. 34 is similar to that of FIG. 20 in that it includes both the recesses 79w, as well as the ridges 93w. In this embodiment, which includes both a distal portion 134, as well as a proximal portion 136 These portions 124 and 136 have a generally common dimension along the axis 77w.

The tip 27x in FIG. 35 includes the conical surface 75x as well as the cylindrical surface 95x. The recesses 79x are oriented generally in respective radial plans. These recesses 79x are similar in shape and have a width which increases toward the distal end 87x.

The tip 27y in FIG. 36 is similar to that of FIG. 19. It includes concentric circular structures at the distal end 85y. In this case however, the structures are a series of recesses 97y rather than ridges. This embodiment includes at least one ridge 93y, however, which extends radially outwardly with progressive proximal positions along the axis 77y.

The tip 27z in FIG. 37 is similar to that of FIG. 35 except that it includes recesses 79z which are fewer in number but wider in size. Also, the nose of the tip 27 at the distal end 85z is accentuated in the embodiment of FIG. 37.

It will be understood that many modifications can be made to the various disclosed embodiments without departing from the spirit and scope of the concept. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments. Those skilled in the art will envision other modifications within the scope and spirit of the present invention as defined by the following claims.

What is claimed is:

1. A surgical obturator comprising:
an elongate shaft having a longitudinal axis extending from a proximal end to a distal end of the shaft; and
a bladeless blunt tip disposed at and extending from the distal end of the elongate shaft; the tip comprising a proximal end and a distal end, and a generally conical outer surface; wherein at least a portion of the outer surface of the tip has a cross-sectional area perpendicular to the longitudinal axis that decreases from the proximal end of the tip to the distal end of the tip; and
at least one recess formed in the outer surface of the tip such that the at least one recess extends radially inwardly from the outer surface generally between the distal end and the proximal end of the tip such that a substantial portion of the at least one recess extends along the tip;
wherein the tip has a blunt distal end with a surface having a cross shape.

2. The obturator of claim 1, further comprising a handle disposed at a proximal end of the shaft.

3. The obturator of claim 1, wherein the obturator comprises a lumen open at a proximal end of obturator.

4. The obturator of claim 3, wherein the lumen is dimensioned to receive a laparoscope therein.

5. The obturator of claim 1, wherein the longitudinal axis extends substantially through the blunt point.

6. The obturator of claim 1, wherein the tip comprises a plurality of recesses.

7. The obturator of claim 1, wherein the at least one recess extends from the blunt distal end.

8. The obturator of claim 1, further comprising a cannula having lumen configured to receive the elongate shaft inside the lumen of the cannula.

9. The obturator of claim 1 wherein the at least one recess deepens relative to the outer surface from the distal end to the proximal end of the tip.

10. The obturator of claim 1 wherein the portion of the outer surface with a decreasing cross-sectional area is a conical surface and the tip includes a cylindrical surface that extends proximally of the conical surface and the at least one recess extends along both the conical surface and the cylindrical surface.

11. The obturator of claim 1 wherein the outer surface of the tip comprises a parabolic surface.

12. The obturator of claim 1 wherein the at least one recess is disposed at an angle with respect to any plane containing the longitudinal axis.

13. The obturator of claim 1 including a plurality of recesses and further including ridges disposed between the recesses.

14. The obturator of claim 1 wherein the at least one recess has an individual width that decreases from the distal end of the tip toward the proximal end.

15. The obturator of claim 1 wherein the outer surface includes a plurality of recesses that extend generally axially from the distal end to the proximal end of the tip.

16. The obturator of claim 1 including a plurality of recesses that extend generally parallel to the longitudinal axis of the tip from the distal end to the proximal end of the tip.

17. The obturator of claim 1 wherein the at least one recess has an angular relationship with the longitudinal axis.

18. The obturator claim 1 wherein the at least one recess extends through the distal end of the tip.

19. The obturator of claim 1 wherein the at least one recess is oriented generally in a radial plane that contains the longitudinal axis.

20. The obturator of claim 1 wherein the at least one recess has a width that increases toward the proximal end.

21. A surgical obturator comprising:
an elongate shaft having a longitudinal axis extending from a proximal end to a distal end of the shaft; and
a bladeless blunt tip disposed at and extending from the distal end of the elongate shaft; the tip comprising a proximal end and a distal end, and a generally conical outer surface; wherein at least a portion of the outer surface of the tip has a cross-sectional area perpendicular to the longitudinal axis that decreases from the proximal end of the tip to the distal end of the tip; and
wherein the obturator includes four recesses formed in the outer surface of the tip such that each recess extends radially inwardly from the outer surface generally between the distal end and the proximal end of the tip such that a substantial portion of each recess extends along the tip; the four recesses extending through the blunt distal end, the blunt distal end having a cross section with the shape of the letter "X".

22. The obturator of claim 21 further including ridges disposed between the recesses.

23. The obturator of claim 21 wherein the recesses have individual widths that decrease from the distal end of the tip toward the proximal end of the tip.

24. A surgical obturator comprising:
an elongate shaft having a longitudinal axis extending from a proximal end to a distal end of the shaft; and
a bladeless blunt tip disposed at and extending from the distal end of the elongate shaft; the tip comprising a proximal end and a distal end, and an outer surface; wherein at least a portion of the outer surface of the tip has a cross-sectional area perpendicular to the longitudinal axis that decreases from the proximal end of the tip to the distal end of the tip; the distal end of the tip is blunt; and
at least one recess formed in the outer surface of the tip such that the at least one recess extends radially inwardly from the outer surface generally between the distal end and the proximal end of the tip such that a substantial portion of the at least one recess extends along a longitudinal axis of the tip;
the tip includes a first cylindrical surface proximal to a conical surface; wherein the at least one recess has a generally constant width along the longitudinal axis of the tip and the at least one recess does not extend into the first cylindrical surface.

* * * * *